US010548695B2

(12) United States Patent
Uckelmann et al.

(10) Patent No.: US 10,548,695 B2
(45) Date of Patent: Feb. 4, 2020

(54) DEVICE FOR THE GENERATIVE MANUFACTURING OF THREE-DIMENSIONAL COMPONENTS

(71) Applicant: Bego Medical GMBH, Bremen (DE)

(72) Inventors: Ingo Uckelmann, Bremen (DE); Simon Hoges, Bremen (DE)

(73) Assignee: Bego Medical GmbH, Bremen (DE)

( * ) Notice: Subject to any disclaimer, the term of this patent is extended or adjusted under 35 U.S.C. 154(b) by 274 days.

(21) Appl. No.: 15/274,834

(22) Filed: Sep. 23, 2016

(65) Prior Publication Data
US 2017/0071707 A1 Mar. 16, 2017

Related U.S. Application Data

(63) Continuation of application No. 15/081,634, filed on Mar. 25, 2016, now abandoned, which is a
(Continued)

(30) Foreign Application Priority Data

Mar. 2, 2011 (DE) .................. 20 2011 003 443 U

(51) Int. Cl.
*B29C 64/00* (2017.01)
*A61C 13/00* (2006.01)
(Continued)

(52) U.S. Cl.
CPC .......... *A61C 13/0019* (2013.01); *A61C 13/20* (2013.01); *B29C 67/0007* (2013.01);
(Continued)

(58) Field of Classification Search
CPC .................... B29C 64/205; B29C 64/245
See application file for complete search history.

(56) References Cited

U.S. PATENT DOCUMENTS 4,759,887 A 7/1988 Geissler et al.
5,354,414 A * 10/1994 Feygin .................. B29C 64/153
264/497
(Continued)

FOREIGN PATENT DOCUMENTS

DE 4102260 A1 7/1992
EP 0734842 A1 10/1996
(Continued)

OTHER PUBLICATIONS

Japanese Application No. 2013-555772, Office Action dated Mar. 15, 2016, 5 pages.
(Continued)

*Primary Examiner* — Timothy Kennedy
(74) *Attorney, Agent, or Firm* — Kilpatrick Townsend & Stockton LLP

(57) ABSTRACT

The invention relates to a device for producing products having individual geometries, comprising a substrate carrier device, a material application device for applying material, preferably above the substrate carrier device, which material application device can be moved relative to the substrate carrier device, and a control device which is coupled to the material application device for signaling. According to the invention, the material application device is coupled to an input interface for signaling and for selection of a first or a second application mode, the control device and the application device being designed such as to produce, in the first application mode, a three-dimensional product on the surface of a substrate plate by way of an additive production method, said substrate plate being connected to the substrate carrier device. According to the additive production method, a curable material is applied in consecutive layers, one or more predetermined regions are selectively cured after or during each application of a layer, the predetermined regions being bonded to one or more regions of the underlying layer.

(Continued)

Figure 1A:
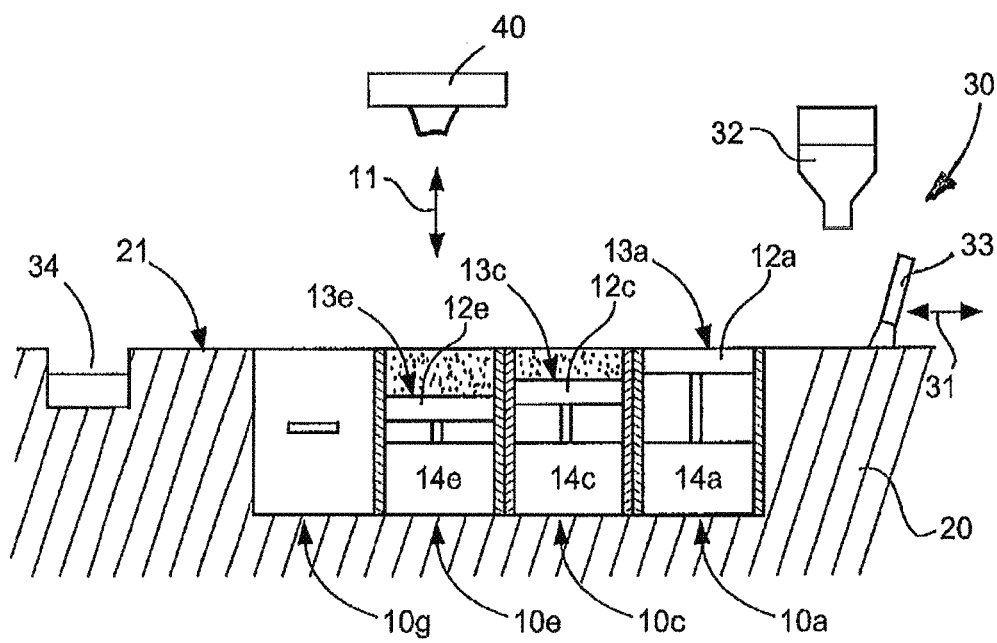

The predetermined region(s) is/are predetermined by a cross-section geometry of the product in the respective layer and is/are stored in the control device, and the curable material is applied in a plurality of consecutive layers to produce the three-dimensional product. The control device and the application device are further designed such that in the second mode of application one or more colors are applied to predetermined regions of a print substrate material connected to the substrate carrier device to produce a monochrome or polychrome print.

11 Claims, 14 Drawing Sheets

Related U.S. Application Data continuation of application No. 13/582,399, filed as application No. PCT/EP2011/065889 on Sep. 13, 2011, now Pat. No. 9,456,884.

(51) Int. Cl.

| | | |
|---|---|---|
| *B29C 67/00* | (2017.01) | |
| *A61C 13/20* | (2006.01) | |
| *B33Y 10/00* | (2015.01) | |
| *B33Y 30/00* | (2015.01) | |
| *B33Y 50/02* | (2015.01) | |
| *B33Y 80/00* | (2015.01) | |
| *B29L 31/00* | (2006.01) | |

(52) U.S. Cl.
CPC ............. *B33Y 10/00* (2014.12); *B33Y 30/00* (2014.12); *B33Y 50/02* (2014.12); *B33Y 80/00* (2014.12); *B29L 2031/7536* (2013.01)

(56) References Cited

U.S. PATENT DOCUMENTS

| | | | |
|---|---|---|---|
| 5,555,481 A | 9/1996 | Rock et al. | |
| 6,165,406 A * | 12/2000 | Jang | B29C 64/165 |
| | | | 264/308 |
| 6,238,614 B1 * | 5/2001 | Yang | B29C 64/165 |
| | | | 264/497 |
| 6,658,314 B1 * | 12/2003 | Gothait | B33Y 30/00 |
| | | | 264/409 |
| 6,989,115 B2 | 1/2006 | Russell et al. | |
| 7,084,370 B2 | 8/2006 | Hagemeister et al. | |
| 7,686,995 B2 | 3/2010 | Davidson et al. | |
| 8,287,794 B2 | 10/2012 | Pax et al. | |
| 9,456,884 B2 | 10/2016 | Uckelmann et al. | |
| 2002/0145213 A1 | 10/2002 | Liu et al. | |
| 2002/0167101 A1 | 11/2002 | Tochimoto et al. | |
| 2003/0003180 A1 | 1/2003 | Farnworth et al. | |
| 2003/0205849 A1 | 11/2003 | Farnworth | |
| 2004/0145639 A1 | 7/2004 | Noutary | |
| 2005/0017394 A1 | 1/2005 | Hochsmann et al. | |
| 2006/0003095 A1 | 1/2006 | Bullen et al. | |
| 2008/0105818 A1 | 5/2008 | Cohen | |
| 2010/0195122 A1 | 8/2010 | Kritchman | |
| 2011/0049739 A1 | 3/2011 | Uckelmann et al. | |
| 2012/0211155 A1 * | 8/2012 | Wehning | A61C 13/0013 |
| | | | 156/275.5 |
| 2013/0026683 A1 | 1/2013 | Ng et al. | |
| 2013/0108726 A1 | 5/2013 | Uckelmann et al. | |
| 2016/0214327 A1 | 7/2016 | Uckelmann et al. | |

FOREIGN PATENT DOCUMENTS

| | | |
|---|---|---|
| EP | 1021997 A2 | 7/2000 |
| EP | 1037739 B1 | 10/2003 |
| EP | 1358855 A1 | 11/2003 |
| EP | 2289652 A1 | 3/2011 |
| JP | 07088967 A | 4/1995 |
| JP | 2000280356 A | 10/2000 |
| JP | 2001239592 A | 9/2001 |
| JP | 2002018967 A | 1/2002 |
| JP | 2008188826 A | 8/2008 |
| WO | 04014636 A1 | 2/2004 |
| WO | 07083372 A1 | 7/2007 |
| WO | 08128502 A2 | 10/2008 |

OTHER PUBLICATIONS

Japanese Application No. 2016-178651, Non-Final Office Action dated Nov. 7, 2017, 5 pages.
European Patent Application No. 18184378.0, Search Report dated Feb. 19, 2019, 5 pages. (no English translation available).

* cited by examiner

DEVICE FOR THE GENERATIVE MANUFACTURING OF THREE-DIMENSIONAL COMPONENTS

CROSS-REFERENCES TO RELATED APPLICATIONS

This application is a continuation of U.S. application Ser. No. 15/081,634, filed Mar. 25, 2016, which is a continuation of U.S. application Ser. No. 13/582,399, filed Jan. 14, 2013, which is the U.S. National Stage of PCT/EP2011/065889, filed Sep. 13, 2011, the content of which are fully incorporated by reference.

This application claims priority of German Utility Model DE 20 2011 003 443U, the content of which is fully incorporated by reference. Further, the content of EP 2289462 A1 and the content of EP 2289652A1 is fully incorporated by reference.

The invention concerns a device for the manufacturing of products with individual geometry, comprising a substrate carrier device, a material application device being movable relative to the substrate carrier device, preferably above the substrate carrier device, and a control unit being coupled to the material application device.

This application claims priority of German Utility Model DE 20 2011 003 443U, the content of which is fully incorporated by reference. Further, the content of EP 2289462 A1 and the content of EP 2289652A1 is fully incorporated by reference.

I. PRIOR ART

Generative production processes, that is production processes in which a material is formed to an individual product in an additive process, find application in the area of prototype production and in the meantime also in the production of products, in particular in the production of individually formed products or low-volume production. A generative or additive manufacturing method according to this description and the appending claims is understood in particular to be any additive manufacturing technique as defined in ASTM F2792-10 to include any process of joining materials to make objects from 3D model data, in particular 3D-printing, fused deposition modeling, selective laser sintering or melting, and stereolitography.

From EP 1021997B1, for example, the manufacturing of individually formed dental prostheses or auxiliary dental parts by a selective laser sintering process with defined parameters is known. The SLS or SLM process is described in principle in EP 0734842 A1, the disclosures of which are considered in their entirety.

In addition to such a selective laser sintering or laser melting process, that is especially suited for dental prostheses (SLS, SLM), for powdered metals, other generative processes can be suitable for other products. Thus, for example, processes in which a granulate or another solid metal are sintered or melted by a high-energy beam, such as a laser beam or an electron beam, and in this way joined and cured, or processes in which a solid or liquid form of a plastic supplied is selectively cured, for example by a high-energy beam such as an electron beam, a laser beam or a focused light beam, by photopolymerization. Other processes and devices relating to the object of the invention function according to a principle by which the material is also applied in consecutive layers, however not as a homogeneous, coherent layer, but as selectively applied layers and the selected regions cured. Such processes are known, for example, as Laser Engineered Net Shaping (LENS) or laser deposition welding.

In another principle relating to the invention the material is also deposited by consecutive layers, as a homogeneous layer or as selectively applied regions of a layer and cured, but does not utilize a high-energy beam. thus, for example, processes are known in which a first material is deposited as a layer and then selectively mixed with and cured with a second material in predefined regions, for example in which a liquid bonding material is injected in the predefined regions or in which the first and second materials comprise a chemically reactive resin+hardener combination. In still other processes, the material is selectively applied only in predefined regions and not as a homogeneous, coherent layer, and therefore hardens by itself. This can be achieved, for example, by applying the material as a chemically reactive or reacting mixture which then hardens by itself or by a chemical reaction, by applying the material in a molten state and curing by cooling or by reacting with the ambient atmosphere, for example air, to form reactive material and curing following the selective application. Such processes relating to the invention are known, for example, 3D printing, contour crafting, fused deposition modeling (FDM), laminated object modeling (LOM), polyamide casting, and multij et modeling.

As a rule, these generative production processes function in such a way that consecutive layers of the curable material are applied to a substrate carrier, for example by immersing the substrate carrier successively and discontinuously in a liquid bath of the curable material or depositing successive layers onto the substrate carrier by means of a powder deposition device. Following each layer deposition process, certain parts of the layer or—as in the case of selective layer deposition—the entire layer is selectively cured and, in this way, the product formed by layers. After finishing the product by curing the last layer, it is possible to remove regions of the material not cured, which can frequently be reused.

A basic problem with the generative production processes is the long time between the creation of the production data and the manufacturing of the product. The simultaneous processing of several products on a substrate carrier in order to increase the number of products manufactured over a certain time is known. Especially for products with very small dimensions compared with the dimensions of the substrate carrier, this procedure is meaningful and effectively enhances productivity.

From EP 0734842 A1 it is known that the downtime of a production device can be reduced with the use of a soluble substrate carrier on a carrier plate and removing the carrier plate immediately following manufacture of the product and replacing with a new substrate carrier in order to start a new manufacturing process. While this design eliminates the downtime required to remove the product from the substrate carrier, this arrangement still has the disadvantage that the production process can be started only when the production data for all products to be manufactured on a substrate carrier, so that, as a result, the overall time for the manufacture of a product cannot be significantly reduced. This is especially true for the individual production of many small products.

From WO 2008/128502 a device is known that follows the same basic ideas and provides for a conveyor device within the manufacturing apparatus with which one or more component holders, as well as dosing or supply containers, can be transported in order to achieve fast, simple and reliable powder handling within the manufacturing device. With this device, products can be manufactured quickly in a component holder by means of powdered material and, following their manufacture, products can be manufactured from a different powdered material. Nevertheless, with this manufacturing device as well, the manufacturing process takes at least as long as between the creation of the production data for all products on the substrate carrier and the manufacturing of the products, so that, in regard to the production of each individual or a number of products formed, a relatively long time is still required.

From WO 2004/014636 a process for the generative manufacture of three-dimensional objects by consecutive layers is known, in which several objects are simultaneously manufactured in two component positions. With this device, a layer is deposited in one position and selective curing is achieved in another region by means of irradiation. Four processing chambers are provided, which can be in the form of spatially separated individual chambers or as subregions of two double chambers or a single four-part chamber. Furthermore, the device incorporates a switching device for connecting a laser to the required processing chamber. The device so characterized and the process described for the generative manufacturing of products with this device have the disadvantage that, for the purpose of simultaneously manufacturing with alternating curing and layer deposition in the respective processing chambers, a separate control unit for the deposition process is required in each of the processing chambers. While the device and the process are suited to the complex special application for manufacturing several products from different starting materials in the respective different processing chambers, the manufacturing process and the device are complex and therefore, with a view to the productivity, the production efficiency for numerous small products and the time required between the availability of the production data of a product and the manufacturing of the product can be further optimized.

II OBJECT OF THE INVENTION

While only individual products, the size of which corresponds roughly to that of the substrate carrier, can be manufactured in both a productive process and an acceptable overall production time with the known production processes and devices, for products having dimensions much smaller than the those of the substrate carrier it is only possible to ensure productivity by the simultaneous manufacturing of several products on a single substrate carrier. In this case, however, the production time for a single product cannot be reduced to the required short time, but increases due to the creation of the production data for all products to be manufactured on the substrate and the simultaneous production which then follows.

Another problem with the generative manufacturing of small products, that is products with a basic surface area smaller, in particular by at least an order of magnitude, than the surface of the substrate carrier, is that in many fields of application with individual product geometries generative manufacturing is carried out as make-to-order production, for example in the manufacture of dental prostheses in dental laboratories. In this case, the different orders are typically not simultaneous, but spread over time for the user of the manufacturing device. In order to achieve high productivity and utilization of the apparatus, the user must combine several orders so as to manufacture the different products simultaneously on the substrate carrier. However, especially for the first order received, this requires a considerable delay between the receipt of the order and the manufacturing of the product. If, on the other hand, the user wants to respond to each order in the shortest possible time, he is then compelled to carry out the manufacturing process on a substrate carrier with only one or only a few products, resulting in the overall poor utilization of the manufacturing device and low productivity.

Another problem with the known production processes and devices is that the maximum dimensions of the products to be manufactured are limited. Above all, this is because the products are manufactured on a substrate carrier, so that, on the one hand, the dimensions of the substrate carrier and, on the other hand, the formation space above the substrate carrier may not be exceeded. We therefore require a device and a process designed to accommodate products having large dimension, especially products in which the extent in one or two spatial directions is much larger in relation to the other spatial direction(s) and efficiently manufacture these products by a generative process.

Yet another problem with the known devices for generative manufacturing is that, as a rule, these devices and the required process control are of complex design and therefore not suitable for inexpensive procurement and utilization. We therefore require a device for generative manufacturing having a simple and compact design and, ideally, that reduced the costs of procurement and utilization.

Still further, we also require a generative manufacturing device that enables higher utilization efficiency for the user and the faster and more cost-effective manufacturing of individual products in a functional and esthetically demanding design.

Finally, the object of the invention is to further develop the known manufacturing processes in such a way that a high productivity and a short production time are achieved for each product, even with products small in size in relation to the dimensions of the substrate carrier. A further objective of the invention is to make a production process and a manufacturing device available that shortens the time between the receipt of an order for an individually manufactured small product and the manufacturing of the product without influencing the productivity of the manufacturing process and the manufacturing device.

III. SUMMARY OF THE INVENTION

Generally, in the description and the appending claims it is to be understood that data required for the manufacturing, i.e. manufacturing parameters and geometric data of single layers/of the product geometry, may be provided from an external control unit, like a computer connected to the manufacturing apparatus, to the manufacturing apparatus or may be generated or stored in a control unit being part of the manufacturing apparatus itself. In the same way it is possible to control and conduct a manufacturing process externally ny way of cloud computing from multiple computers connected to each other and communicating with each other.

III.1 First Embodiment: Apparatus and Method for Conducting an Additive Manufacturing Process with Oblique Layer This problem is solved according to a first aspect of the invention by a device mentioned above, in which the control device is adapted to control the material application device in such a way that it dispenses the material selectively on predetermined regions corresponding to the cross-section of the product in the respective layer, and the material application device is adapted to apply the material in a plane, which is oriented oblique, in particular in an angle being smaller or equal to the dumping angle of the material, to the surface of the substrate plate, which the material is applied on.

With a device according to the present invention, a generative manufacturing device is proposed, which can manufacture small products in a fast way with high productivity. The device according to the present invention is characterized in that the material application device, with which the material layers are applied on the substrate plate, is designed in such a way that the layer application can be executed oblique to the surface of the substrate plate.

Under the term "oblique application" it is to understood that a pointed angle is adjustable between the application plane and the surface of the substrate plate, which can lie in particular between and including 0 and including 90°, preferably being smaller than 90° and/or greater than 0° and in particular having a lower limit of 5°, 10° or 30° and/or an upper limit of 60°, 80° or 85°.

An essential element of the method executed with the device according to the present invention, is the curable material, which is applied and subsequently cured. The material must be suited to be employed in a layer application oblique to the surface of the substrate plate, but at the same time achieve a sufficient geometric resolution of the product details. Specifically adapted powders, powder mixtures, alloyed powders, liquids with predetermined viscosity or pasty materials or granulates can be employed as materials herefore. In the meaning of this description a curable material is understood to be a material which is adapted in one manufacturing condition to be homogeneously or selectively applied as a thin layer and which is curable. The curable material must be further adapted to be joined to a previously applied layer and optionally with adjacent layer regions of the applied layer to establish a connection able to be mechanically loaded. This mechanical connection will often be established in the course of the process of curing of the material. The curable material thereby takes the role of providing structural mechanical function of the product. The curable material may be transparent or coloured. The curable material is applied according to the present invention alone, as a mixture of two or more materials at the same time or time-delayed consecutive by means of a material application device.

This material application device is accordingly adapted to obtain the material from a material source and to establish a suited dispensing form for the material and then to dispense one or a plurality of materials at the same time or time-delayed in form of a jet, powder, in form of balls, drops, stripes, larvals or the like. In a simplified embodiment the material application device is arranged at a frame and said frame can be arranged such on a surface that a movement of the frame in one, two or three axes relative to said surface is provided. As an example, the surface may a surface of a table whereupon the frame is supported in a rolling manner. The surface then represents the substrate plate. The movement between the material application device and the surface can in particular be provided by a combination of the movement of the material application device relatively to the frame in one or more axes and a movement of the frame relatively to the surface in one or more axes supplementary to these.

Under the term "curing" it can be understood herein a melting and a subsequent solidification of a material existing in form of a wire, particle or powder, even so a molten application of a material with consecutive solidification. The curing can also be carried out by chemical reaction of a material with the environment, chemical reaction of two or more material components being applied at the same time or time-delayed with each other or chemical or physical reaction of a material as s result of a radiation impact, for example as a photopolymerization.

According to a first preferred embodiment, the device according to the present invention comprises a radiation source for a high-energetic radiation, and radiation guiding means for directing the radiation onto a predetermined region of a material layer applied on the substrate plate. With this embodiment in particular generative manufacturing methods such as SLS, SLM, application welding, LENS or stereo-lithographic methods can be executed.

The device according to the present invention can be further advanced, by dividing the substrate plate into a plurality of substrate plate segments and by adapting the material application device to simultaneously apply a material layer onto a number of the plurality of substrate plate segments.

Even further the device according to the present invention can be advanced by connecting the substrate plate segments detachable with each other or detachable with a base carrier.

Furthermore, it is preferably provided that the substrate plate segments are arranged at an endless conveyor belt running partially or completely in a processing chamber, which is sealed against the environment as far as therein a controlled, in particular inert atmosphere, can be adjusted, and that preferably the material application device is designed in such a way that the material can be applied in a first direction, preferably in such an angle to the surface of the respective substrate plate segment that the flowing direction of the material is opposite to the application direction.

The device according to the present invention can be further adapted by a control for controlling the radiation guiding means of the high-energetic radiation and/or the material application device, which is adapted to control the radiation guiding means and/or the material application device in such a way that a dividing wall is manufactured during the manufacturing process of the product by curing the applied material or selectively applying the material, respectively.

A further preferred embodiment provides that the substrate plate segments and the material application device are movable individually relative to each other in such a way that the maximum space between a first substrate plate segment and a material layer being applied above this substrate plate segment for manufacturing a first product differs from the maximum space between a further substrate plate segment and a material layer being applied above this further substrate plate segment for manufacturing of a further product.

A further preferred embodiment is characterized by a material detaching device, in particular a material suction device, wherein the material detaching device is adapted to detach a non-cured material from the circumferential region of a manufactured product, and the material detaching device being preferably arranged in such a way that it detaches the material surrounding a completed product on a first substrate plate segment and thereby leave the material surrounding a product on a further adjacent plate segment.

Even further it is preferred, if the device according to the present invention includes a control for controlling the guiding device of the high-energetic radiation and/or the material application device, which is adapted to control the guiding device an/or the material application device in such a way that in a first phase of the manufacturing process only layer regions of the layer are selectively cured, which serve for manufacturing of a first product on a first substrate plate segment, in a last phase of the manufacturing process, only layer regions of the layer are selectively cured, which serve for manufacturing of a further product on a further substrate plate segment and in a middle phase of the manufacturing process lying between the first and last phase layer regions of the layer are selectively cured, which serve for manufacturing of the first and the further products.

According to a further preferred embodiment the device according to the present invention comprises a dividing wall being arranged between the substrate plate segments, wherein the dividing wall divides the existing available space above each substrate plate segment from the existing available space above an adjacent substrate plate segment.

Therein it is particularly preferred if the dividing wall between two substrate plate segments is connected to at least one of the two substrate plate segments or sealed against this substrate plate segment in such a way that no material can pass between the dividing wall and the substrate plate segment.

Especially preferred, the device according to the present invention comprises a single radiation source, which particularly is used by means of a single optical path for curing all products, in particular of the products being manufactured on all substrate plate segments.

Even further it is preferred to provide a control for controlling the guiding device of the high-energetic radiation and/or the material application device, which is adapted to guide the energetic radiation and/or the material application device over the n-th material layer based on guiding data, which have been determined from the geometric data of a x-th cross-sectional area of a first product for curing parts of the n-th material layer by means of acting of an energetic radiation or selective material application, respectively, to guide the energetic radiation and/or the material application device over a n+1-th material layer based on guiding data, which have been determined from the geometric data of a x+1-th cross-sectional area of the first product to cure parts of the n+1-th material layer by means of acting of the energetic radiation or selective material application, respectively, to guide the energetic radiation and/or the material application device over the n-th material layer based on guiding data, which have been determined from geometric data of a y-th cross-sectional area of a second product to cure parts of the n-th material layer by means of acting of the energetic radiation or selective material application, respectively, and to guide the energetic radiation and/or the material application device over the n+1-th material layer based on guiding data, which have been determined from the geometric data of a y+1-th cross-sectional area of the second product to cure parts of the n+1-th material layer by means of acting of the energetic radiation or selective material application, respectively, wherein x is not equal to y.

According to a further embodiment, it is provided that the relative movement between the substrate plate and the material application device is achieved partly or completely by means of a conveyor device, which executes a conveying movement along at least one axis or, if applicable, along two or three axes and which can be furthermore designed swivelable about one, two or three axes. The conveying device can in particular comprise one or a plurality of conveying belts, which can be controlled simultaneously or independently from each other to manufacture products thereon. The conveying device can comprise a receiving device for receiving of substrate plates or include a surface serving directly as a substrate plate surface, for example a conveying belt surface. The plurality of conveyor belts can be aligned adjacent to each other in a plane or can be arranged in such a way that they limit an available space from beneath, at the sides and/or from above to achieve thereby an even conveying of the material.

It is furthermore preferred that the substrate plate and/or an actuator interacting with the substrate plate is designed to be moved in a horizontal direction at each build-up of a new layer. This way of movement in connection with the oblique layer orientation and a horizontal substrate plate provides for the advancement required for application of a new layer, wherein said advancement multiplicated with the sinus of the application angle determines the layer thickness.

It is furthermore preferred that the material application device is guided in such a way that it is movably supported in a plane, which is oriented oblique to the surface of the substrate plate.

The device according to the present invention can be enhanced by a second material application device, which is designed and movable to apply a second material as a homogeneous layer before a selective material application takes place.

It is furthermore preferred, that the material application device is designed to apply a material mixture of two different materials, wherein the two different materials are designed to cure with each other after the selective application by a chemical reaction, or to apply a material selectively, wherein the material is designed to cure after the selective application by chemical reaction with an environmental gas, or apply a molten material selectively, wherein the molten material is adapted to cure after the selective application by cooling down.

It is furthermore preferred that the material application device(s) is/are arranged and designed in such a way with respect to the substrate plate and the direction of gravitation in operating position that the material dispensed therefrom can be fed in gravitational direction as a layer onto the substrate plate or onto layers arranged thereon or on predetermined regions of the substrate plate, respectively, or layers arranged thereon.

Finally, the device according to the present invention can be characterized in that a processing device is arranged at the material application device for baring of a part of the cured material regions, preferably for skin-deep grinding of the cured material regions of a beforehand applied material layer.

A further aspect of this embodiment is a method for manufacturing of products with individual geometry, in particular tooth replacement or dental parts, with the steps: manufacturing of at least one product at or on a surface of a substrate plate by means of selective curing, in particular by means of selective sintering or melting, applying a curable material in consecutive layers, selective curing of one or a plurality of predetermined regions after each layer application and thereby connecting these regions with one or a plurality of regions of the underlying material, wherein the predetermined region(s) are predetermined based on a cross-sectional geometry of the product in the respective layer, and wherein the material is applied selectively in the predetermined regions of the layer, and wherein the consecutive layers are applied in layer planes being oriented oblique to the surface of the substrate plate.

The device according to the present invention preferably works further according to a method for manufacturing or products with individual geometry, in particular tooth replacement or dental parts, with the steps of manufacturing a plurality of products on the surface of the substrate plate by means of selective curing, in particular by means of selective sintering or melting, in which the material is applied in consecutive layers, wherein after each layer application one or a plurality of predetermined regions of the applied layer are selectively cured, preferably by means of an energetic radiation and connected with one or a plurality of regions of the underlying layer, wherein the predetermined regions are determined in the respective layer based on a cross-sectional geometry of the product, in which the consecutive layers are applied in layer planes, which are oriented oblique to the surface of the substrate plate.

Also in this method, one or a plurality of products are manufactured layerwise at the same time on the surface of a substrate plate by a selective curing process. In this respect, it is to be understood that in the method according to the present invention not necessarily a substrate plate of classic design, i.e. a circular, quadratic or rectangular one-part substrate plate, has to be employed. Instead of that, the substrate plate according to the present invention can be provided for example as a substrate conveyor belt or as a substrate plate being composed of a plurality of segments, in which these substrate plate segments are aligned for example along one direction.

The method is characterized in that the layers of the cured material are not applied in such a way that the layer planes are aligned parallel to the surface of the substrate plate, but instead are applied in such a way that the layer plane is aligned oblique, i.e. with an angle between 0° and 90° to the surface of the substrate plate. By this oblique layer application on the substrate plate it is achieved that the material bed thickness arranged within one location of the substrate plate is not equal at each position, but varying. In particular, the thickness of the applied material bed enlarges proceeding from a region, in which exactly one layer thickness lies on the substrate plate, continuously to a region, in which the maximum applicable layers can be laid upon the substrate plate. Herein it is to be understood that a material layer is always applied above a region of the substrate plate, which in fact does not necessarily have to coat the whole substrate plate, but usually coats a region, in which a plurality of products are arranged being built on the substrate plate.

By the oblique application of the material layers, a plurality of small products can be built on the substrate plate by the method according to the present invention, which, however, are in different manufacturing stages. Thereby in a region, in which by the oblique application of the layer only one single layer lies on the substrate plate, a new product can be started, wherein in a region, in which the oblique applied layer is applied on a plurality of before-hand applied layers, a product can be completed. Between both of these endpoints, one or a plurality of products can be arranged in a manufacturing stage between beginning and end, i.e. with for example 50 or 100 already applied and selectively cured layers.

This manufacturing method establishes thereby to start directly after completion of the manufacturing data for a product the manufacturing of this product and then to withdraw this product after completion from the manufacturing process, without having to wait herein that the manufacturing data of other products have been completed, or even that other products have been completed. Herein it is to be understood, that in the same way as in a quasi-continuous manufacturing start of consecutive individual products in the method according to the present invention, it is realized that a quasi-continuous withdrawal of single-completed products can be established to minimize the manufacturing time for each single product. By the method according to the present invention, it will be thus possible to manufacture also products with small dimensions in such a manufacturing time, which is only needed by the process steps being necessary for the single layer applications and their curing and at the same time achieve a high productivity by a parallel manufacturing of a plurality of products, by achieving by an oblique material or powder application with respect to the substrate plate to manufacture products in different manufacturing stages on a substrate plate and with a common layer application. The material or powder application preferably takes place along one direction, which is opposite to the flowing direction of the powder in the layer being influenced by the gravitation if the layer is oriented oblique to the horizontal.

According to a first preferred embodiment, it is provided that the consecutive layers are applied parallel to each other. By the parallel application of the layers, an equal layer thickness along the whole application process and thereby a simple process control is achieved. Herein it is to be understood that not necessarily each of the layers has to obtain the same layer-thickness in particular the layer thickness can be selected greater or smaller depending on the product geometry to adapt the geometric resolution of the product geometry being determined by the layer thickness.

Furthermore, it is preferred that a plurality of products is manufactured on the surface of the substrate plate by means of selective curing, in particular by means of selective sintering, melting or application, and that preferably the one or the plurality of predetermined regions is cured by means of an energetic radiation or selective material application and thereby connected with one or a plurality of regions of the underlying layer.

According to a further preferred embodiment it is provided that each of the consecutive layers is applied in an angle being smaller or equal to the dumping angle of the material on the substrate plate. In principle, herein the angle, in which the layer is applied, is to be understood as the angle, which is included in the pointed angle between the plane of the surface of the substrate plate and the plane of the applied layer. Under the term "dumping angle" of the material that angle is to be understood which adjusts itself between the side surface of a material hill and a base surface which the material is applied on by way of dumping. The dumping angle of a material is even smaller the greater the sliding ability of the material on the surface which it is applied on and the higher the sliding ability of the material in itself, also for example, the sliding ability of the single powder grains of a powder-formed material with each other. If the consecutive layers in the method according to the present invention are applied in an angle being smaller or equal to the dumping angle, it can be secured in this way that an applied layer does not lose its applied geometric form afterwards by slipping down from layer parts or single material particles or the like. Instead it is secured by the selection of such an application angle that the layer keeps lying stable as a free dumping and consequently can be selectively cured in a simple and geometrically precise way.

To influence the dumping angle positively, i.e. to achieve a possibly great dumping angle and consequently to be able to apply also the layers in a possibly great angle, on the one hand the surface of the substrate plate can be treated in a specific way, for example by polishing, grinding, lapping, honing, bating, tumbling, sand-blasting, milling, turning and other treating methods such as for example a structuring of the substrate plate surface by selective material application of the cured material in form of a regular or irregular lattice structure, point structure, line structure or the like, which further preferably is of a microscopic measure with structure dimensions under 1 mm or of a microscopic measure with structure dimensions above 1 mm. Alternatively or additionally, the substrate plate surface and/or if applicable, the structuring formed thereon, is coated with an adhesive, to improve the footing of the material and of the additively manufactured products. Accordingly, a manufacturing device according to the present invention can include a control device for establishing such a structuring and/or an application device for applying such an adhesive. Herein, the manufacturing method can be preferably adjusted in such a way that a roughness of the substrate plate is achieved being favourable for a great dumping angle, which typically lies in the region from 0.5 µm to 50 µm $R_z$ (the averaged roughness depth according to DIN EN ISO 4287:1998), or typically in the region from 0.1 µm to 10 µm $R_a$ (mean roughness value) or in the region from 0.04 mm to 1.3 mm $R_{sm}$ (averaged groove width according to DIN EN ISO 4287:1998 in periodic profiles, as to be found for example in milling). Therein, it is to be understood, that these preferred roughness regions of the substrate plate are typically advantageous for powders, which are employed for the selective laser sintering or selective laser melting, in particular to manufacture thereby small parts being true to form and precise such as dental implants or parts.

Further preferably the surface of the powder can be processed by polishing, grinding, bating, sand-blasting, tumbling or coating to influence the dumping angle in the above mentioned sense in a positive way.

So far as liquid materials are employed as curable materials, the wettability of the surface can be influenced positively by a chemical, optical or mechanical surface treatment, such as for example laser radiation roughening.

A further approaching point to influence the dumping angle in the above mentioned sense in a positive way is the mentioned granulation of the material. This can take place for example by casting melted metal in a thin jet into cold water under continuous stirring to achieve thereby granulated material. One can granulate other easily meltable metals by casting them into a can being coated on the inner wall strongly with chalk and shaking the can after closing until the metal is cooled-down.

Therein it is in particular advantageous for the method and the device according to the present invention, if the material is prepared in such a way that a good connection, cramping or the like of the material particles with each other and a respective bed sliding ability of the particles on each other, is achieved, i.e. the particles should in particular have an outer shape being different from the sphere, at the same time have a high surface roughness and in particular preferably further be of overall irregular shape. The sliding ability of the material influences at the same time its applicability to be applied in these layers and to form a contact package with small portions of hollow space. The material must also be prepared in such a way that on the one hand a maximum dumping angle is achieved. On the other hand, the materials must be applicable in layer thicknesses suitable for the process and achieve a possibly high package compactness, since this is in direct coherence with the achieved compactness of the manufactured products. Typical layer thicknesses lie between 5 µm and 200 µm.

According to a further preferred embodiment, it is provided that the substrate plate is moved between two consecutive layer application processes with a direction component perpendicular to the plane in which the layer is applied. Under the term "direction component" it is to be understood in this context a portion of movement which together with other movement portions occurring in other directions constitutes to an overall movement. By a movement portion perpendicular to the plane of the layer application an advance can be established, which achieves a subsequent layer application without having to move therefore the layer application device in another way than parallel to the plane of the layer application. In particular, this direction component can be achieved by moving the substrate plate in a direction parallel to the surface of the substrate plate. Such a movement includes because of the angle between the surface and the plane of the layer application, the direction components necessary for the advance necessary for the consecutive layer application.

It is in particular further preferred, that the surface of the substrate plate proceeds in the region, in which the layers are applied, horizontally with respect to the gravitation. In this case the layer is applied in a plane, proceeding oblique to the horizontal and the layer application device has to be adapted for such a layer application proceeding oblique to the horizontal.

In an embodiment alternative hereto, it is provided that the surface of the substrate plate is aligned oblique to the horizontal with respect to the gravitational direction in the region in which the layers are applied. By the surface of the substrate plate aligned oblique to the horizontal in the layer application region it is achieved that the layer is applied in a horizontal plane. The layer application device can be adapted accordingly for a movement in a horizontal plane. Therein it is to be understood that even if the substrate plate is aligned oblique to the horizontal, also a material application proceeding oblique to the horizontal, can be carried out and the material application device can be adapted accordingly.

In both the before-hand mentioned embodiments, it is further preferably provided that the applied layers are moved in a manufacturing section lying adjacent to an adjacent manufacturing section, in which the layers are applied, and being designed as a clamping area, the adjacent manufacturing section, in which one upper surface of the applied material being formed by the applied layers, is covered and supported by a surface of a cover plate being parallel to the surface of the substrate plate. In this embodiment, a support of the material takes place in a predetermined manufacturing section, in which the height of the material above the substrate plate reaches a predetermined height, by the substrate plate on the one hand and the cover plate on the other hand. The distance between the substrate plate and the cover plate thereby corresponds to the maximum height of the layer bed, i.e. the number of layers multiplied by the layer thickness. By providing such a cover plate, the material can be stabilized on the substrate plate in a favourable way, and thereby the oblique layer application can be achieved in geometrically precise and reproducable way. The cover plate herein comes into contact with each of the end sections of the material layers pointing away from the substrate plate and supports these. Therein it is to be understood that the cover plate can be designed also in form of an endless conveyor belt or a movable plate moving synchronously with the movement of the substrate plate. In this way, a relative movement between the applied material and the cover plate is avoided, which would otherwise cause a disturbance of the even layer application in the boundary region of the cover plate.

According to a further preferred embodiment, the surface of the substrate plate is divided into a first surface of a first substrate plate segment and at least one further surface of a further substrate plate segment. In this enhanced embodiment, the substrate plate is divided into two or a plurality of adjacent substrate plate segments. Under the term "substrate plate segment" it is herein to be understood a manufacturing-orientated separate section of the substrate plate, which can solely be defined by the control data of the layer application and the curing sequence. In this case, a substrate plate segment forms the region of the substrate plate, on which one or a plurality of products are manufactured, which can be withdrawn at the same time from the substrate plate, since they are started and completed quasi at the same time. Under the term "substrate plate segment" it can be understood in particular also a physically separate building element. In this case, the substrate plate is put together by a plurality of joined segments. The segments can in this case also be employed to build on each segment one or a plurality of products, which are started and completed quasi at the same time and then can be detached from the substrate plate segment.

Herein, it is in particular preferred if the substrate plate segments are connected detachable with each other or detachable with a base carrier and each substrate plate segment is detached from an adjacent substrate plate segment or the base carrier after manufacturing of one or a plurality of products on its surface to feed the product(s) arranged thereon to further process steps. By this enhanced embodiment it is achieved to withdraw each substrate plate segment from the manufacturing device to feed the completed product arranged thereon to further process steps. Such further process steps can be for example an accurate separation of the product from the substrate plate segment, a machined post-processing, an additional curing and the like.

Even further, it is therein in particular preferred if the substrate plate segments in the manufacturing section, in which the layers are applied, are provided adjacent to each other in such a way that no material can pass between the substrate plate segments. The provision of substrate plate segments being executed in such a way, is in particular of advantage if layers are applied with one single layer application device beyond a plurality of substrate plate segments in one process step. In this case, it is avoided that material from one layer application can pass between the substrate plate segments, which could on the one hand lead to unfavourable material loss and on the other hand a geometric influence of the layer thickness and the layer distribution. This can be achieved for example by the substrate plate segments with congruent rim regions arranged directly together and by a respective separate sealing arranged between two substrate plate segments.

Even further it is preferred that the substrate plate is designed as an endless conveyor device, in particular the substrate plate segments are designed as segments of an endless conveyor device. The substrate plate segments can be for example attached to an endless conveyor belt or can be connected in such a way with each other that they form such an endless conveyor belt in form of a link chain. In this case, the substrate plate segments can be moved in consecutive way along an upper branch and a lower branch, wherein the layer application and the selective layer curing take place during the movement along the upper branch. The removal of non-cured applied material from the space between the manufactured products and the removal of the products can also take place in the region of the upper branch, for example by respective suction devices or mechanical dividing devices, respectively. However, it is possible in the same way to let the removal of the non-cured material take place in the region of the lower branch or in the transition from the upper branch to the lower branch, for example due to gravitation and the completed products can then be removed either together with a substrate plate segment or directly from the substrate plate segment in the region of the lower branch.

According to a further preferred embodiment, it is provided that the substrate plate segments are designed and arranged in such a way that a first product or a group of first products is built on a single substrate plate segment and that a further product or a group of further products is built on a further or a plurality of further substrate plate segments. In this embodiment, on the one hand one or a plurality of products can be manufactured on a single substrate plate segment to manufacture in this way with high productivity small products in a very fast manufacturing time. On the other hand, it is also possible to manufacture a single product on a plurality of substrate plate segments. This can be in particular advantageous if greater products are to be manufactured by the method according to the present invention, thus such products having a longitudinal extension or contact surface being greater than the surface of one substrate plate segment. Even further it is provided that a group of a plurality of products can be manufactured on two or more substrate plate segments. This can in particular be necessary in products, which only extend very far in one certain direction. Thereby, with the method according to the present invention, a product can be manufactured, whose length reaches beyond a plurality of substrate bed segments. If a plurality of such products are to be manufactured, then according to this enhanced embodiment, a group can be manufactured, which is formed by such products and this group extends beyond a plurality of substrate plate segments.

The method according to the present invention is in particular characterized in that the material is applied as a continuous layer on the first and at least a further substrate plate segment and selectively cured in such a way that the maximum space between the first substrate plate segment and the layer section being applied thereon for manufacturing the first product differs at least in one, preferably a plurality, in particular all method stages from the maximum space between the further substrate plate segment and the layer section being applied thereon for manufacturing the further product. With respect to the method according to the present invention, the material exists at least in one method stage of the manufacturing in such a way that the space between a first substrate plate region and the layer applied above this region is greater than the space between another substrate plate region and the layer applied above these other regions, wherein this layer is the same layer as the one mentioned before. Even further, the method according to the present invention can be enhanced by the steps: removing of material being arranged on the first substrate plate segment, which has not been cured without thereby removing material of a further substrate plate segment, and subsequently removing material arranged on the further substrate plate segment, which has not been cured. For the quasi-continuous generative manufacturing according to the present invention, it is in particular advantageous at the withdrawal place, if the removal of the non-cured material ca take place in such a way that an adjacent region is not influenced thereby and the non-cured material in this adjacent region stays there. During the generative manufacturing, the non-cured material has a supporting function and serves to receive and support overlying layers. The non-cured material generally must not be removed before the product has not been completely built and cured. However, to avoid under such a requirement the necessity for the completed products having to cover a longer distance serving for the process security until they reach the removal place at which the non-cured material is removed, it is advantageous if the material removal device can achieve the material removal without influencing the directly adjacent region. This allows for the fast and quasi-continuous manufacturing and avoids the provision of a safety distance between the layer application device and material removal device.

Even further it is preferred that in a first phase of the manufacturing process, only layer regions of one layer are selectively cured, which serve for manufacturing of the first product and in a last phase of the manufacturing process only layer regions of one layer are selectively cured, which serve for manufacturing of the further product and preferably in a middle phase of the manufacturing process lying between a first and last phase layer regions of one layer are cured, which serve for manufacturing the first and the further product. By the quasi-continuous and simultaneous manufacturing of products in different manufacturing stages achieved in this way, an efficient and fast method for individual manufacturing of small products by means of a generative manufacturing method is achieved.

Even further it is preferred if between the substrate plate segments a dividing wall is provided, which divides the available space existing above each substrate plate segment from the space existing above an adjacent substrate plate segment. Such a dividing wall allows for and simplifies the removal of non-cured material above a substrate plate segment without thereby influencing the non-cured material in an adjacent substrate plate segment hereto. Herein it is to be understood that such a dividing wall can be provided as a part of the manufacturing device and in this case for example designed in such a way that it is simultaneously tracked according to the layer application to have at any one time the exact height or little less than the exact height of the material application in the region between two substrate plate segments.

According to a herein preferred embodiment it is provided that the dividing wall is manufactured by curing the applied material during the manufacturing of the product(s). With this enhanced embodiment such a dividing wall is manufactured from the applied material at each border of a substrate plate segment during the manufacturing process. This approach provides the advantage that constructively complex dividing wall trackings are not necessary. Instead a respective dividing wall is built along the border region of a substrate plate segment, which can then be removed during the removal of the products from the substrate plate segment or is removed in the course of the removal of non-cured material from the adjacent substrate plate segment.

Therein it is in particular preferred if the dividing wall between two substrate plate segments is connected with at least one of the both substrate plate segments. By connecting the dividing wall with both substrate plate segments, which divides them from each other, at the same time also a secure sealing against material passing between the substrate plate segments is achieved. The connection can herein be achieved by generative build-up of the dividing wall on one or both substrate plate segments or by respective constructive connection of a dividing wall building element belonging to the device.

According to an even further preferred embodiment, it is provided that the material is applied in a first manufacturing section in a quasi-continuous method on the substrate plate and selective predetermined regions of each applied layer are cured and in a second manufacturing section completed cured products are removed quasi-continuously. By this embodiment, a quasi-continuous generative manufacturing process is executed, which is characterized by high productivity and at the same time that also very small products in a very short time interval can be manufactured generatively. This manufacturing way allows for a qualitatively high-valued generative manufacturing in a first manufacturing section and at the same time a removal of completed products in a second manufacturing section not negatively influencing the generative manufacturing, wherein the second manufacturing section is spaced apart from the first manufacturing section. This can in particular be achieved by means of an endless conveyor belt, on which the substrate plate segments are arranged, or which is formed by substrate plate segments. In particular, in this embodiment, the first manufacturing section can be held in a closed inert atmosphere to be able to adjust the boundary conditions necessary for a generative manufacturing according to a certain method, whereas the second manufacturing section allows for an export of the products or the products are exported already at the transition from the first to the second manufacturing section from the inert atmosphere.

Even further it is preferred that before each material application, the cured regions of the before-hand applied layer are grinded skin-deep. By such a surface treatment, which in particular takes place by grinding, but also by other cutting manufacturing methods with geometrically defined or geometrically undefined blade, the geometric precision of the generative manufacturing method is further enhanced. In particular by such a cutting treatment a defined contact area and connection place is provided for the overlying layer and the regions to be cured therein. Additionally, by the cutting treatment a defined layer thickness is adjusted, which is of advantage for a reproducable geometric manufacturing outcome.

Even further it is preferred that for the curing of the product(s) on the substrate plate, in particular on all substrate plate segments, one single radiation source, in particular a single optical path of one single radiation source is used. Generally it is to be understood that for accelerating the manufacturing process also a plurality of radiation sources or a plurality of optical paths of one single radiation source can be employed. The manufacturing method according to the present invention is in particular characterized in that indeed a plurality of products is manufactured at the same time and these products are in different manufacturing stages, i.e. in particular built-up with a different number of layers. However, it is herein unique that not only the application of a layer can take place by one single layer application device for all substrate plate segments and the built-up products to be manufactured thereon and that in addition also the curing of the certain regions of one layer can take place for all the products to be manufactured by one single radiation source.

Finally, the method according to the present invention can be further improved by the steps: selective applying of a material layer or applying of a n-th material layer on a substrate carrier plate and selective curing of parts of the material layer by means of acting of an energetic radiation, in particular a laser radiation, on these parts of the material layer, guiding the energetic radiation or a material application device, respectively, over the n-th material layer based on guiding data, which have been determined from the geometric data of a x-th cross-sectional area of a first product, selective applying of a material layer or applying of a n+1-th material layer on the n-th material layer, guiding of the energetic radiation or a material application device, respectively, over the n+1-th material layer based on guiding data, which have been determined from the geometric data of a x+1-th cross-sectional area of the first product, guiding of the energetic radiation or a material application device, respectively, over the n-th material layer based on guiding data, which have been determined from the geometric data of a y-th cross-sectional area of a second product, and guiding the energetic radiation or a material application device, respectively, over the n+1-th material layer based on guiding data, which have been determined from geometric data of a y+1-th cross-sectional area of a second product, wherein x is unequal to y. In this preferred embodiment at least two products are manufactured by undergoing a selective curing in a common layer application in two different layer regions of one single layer, wherein in this layer in the products themselves different heights with respect to the substrate plate are constituted.

III.2 Second Embodiment: Apparatus and Method for Conducting an Additive Manufacturing Process and a Two Dimensional Print Process The basic purpose of the invention is satisfied by another aspect of the invention by a device for the manufacturing of products with individual geometry, in particular dental prostheses or dental parts, comprising a substrate carrier device, a material application device being movable relative to the substrate carrier device for application of material, preferably above the substrate carrier device, a control unit being coupled to the material application device for transmitting signals, characterized by an input interface being coupled to the control unit for selecting between a first and second application mode, and characterized in that said control unit and said application device are designed to manufacture a three-dimensional product in the first application mode by means of an additive manufacturing method on the surface of a substrate plate being connected to said substrate carrier device, by applying a curable material in consecutive layers, selectively curing one or more predetermined regions after or during each layer application and thereby connecting these predetermined regions with one or more regions in the underlying layer, whereby the predetermined region(s) are defined on the basis of a cross-sectional geometry of the product in the respective layer and stored in the control unit, and the curable material is applied in a number of consecutive layers for manufacturing the three-dimensional products, and in the second application mode by the application of one or more colors to predetermined regions of a print carrier to obtain a single-colored or multi-colored print.

According to this aspect, the invention is directed to a method and a device for additive manufacturing in combination with a method and a device for black and white or color printing. The apparatus is characterized in that in a first mode a material application takes place wherein the material is applied in a layer-by-layer fashion and consequently a connection between an applied layer and a previously applied layer is established. The material application device is adapted for application of a material adapted for this process.

In the second application mode, however, a color is applied to a print medium. This color is not necessarily adapted to establish a connection with each other or to cure but is characterized by color fidelity and color brilliance. In this context a color in the meaning of this description and the claims is meant to be a colored material having a process consistency allowing its application by an application device, for example a liquid like ink of an ink jet printer or toner of a laser printer. The color is characterized in that it substantially does not establish a projecting or embossed structure on the print medium but in particular is taken up party or completely by the print medium for fixing the print image.

With the proposed device, an additive manufacturing device is suggested which, on the one hand, gives the user more freedom in the esthetic design of the products manufactured and, on the other hand, allows universal applications. The device is characterized first by enabling the generative manufacturing of three-dimensional products by forming these according to consecutive layers, Furthermore, an additive manufacturing process is used that can function according to different production principles. In principle, additive manufacturing processes can be used, in which a homogeneous layer is first applied and then predetermined regions of this layer are selectively cured, for example by the correspondingly selective application of another material for the setting of the material in the homogeneous layer in the selected region or by the effect of selectively irradiating regions with the aim of sintering, melting or photopolymerization of the material in the homogeneous layer in these regions. Especially preferred for the device characterized here are however processes in which selective layer deposition already takes place, that is the material is selectively applied only in predetermined regions and these selective regions then cured. These also include such processes as multijet modeling, fused deposition modeling and 3D printing technologies, in which chemical etching or physical changes of state transform a material from a powdered form, liquid, paste or other processed state to a solid, cured state.

For all designs of the device, curing is understood to mean the structural solidification of the material in the predefined geometrical dimensions with the simultaneous bonding of the selectively cured regions to the adjacent regions of the same layer or the already cured regions of an adjacent layer.

The invention is therefore characterized especially by being designed in such a way that, in addition to such additive manufacturing processes for a three-dimensional product, conventional printing in two-dimensional form is also possible. This two-dimensional printing is, in principle, implemented for said second mode in such a way that a printing material is selectively applied to a print carrier, for example as known from printing devices according to the ink jet principle or the laser jet principle with the selective application of color by means of a printing head or a print roller. In principle, the invention characterized here and the respective printing technology can be implemented, in particular for black and white printing or color printing by making the required printing materials available but is inter alia characterized in that the substrate carrier device is adapted for conducting the first application mode and can be controlled correspondingly.

The specific combination of the possibility to manufacture three-dimensional products with the device, on the one hand, and the possibility of conventional printing to a print carrier, such as paper, film, etc., on the other hand, represents advantageous synergy, in that different component can be used for both production processes, ultimately leading to savings in terms of costs and space for the user. To this extent, the invention characterized incorporates an advantageous combination of two production processes which call upon common components in a specific way and therefore result in a compact and cost-effective design of the device. Furthermore, the interaction of the first and second application modes also enables the printout and consequently makes a three-dimensional product view in two-dimensional form available from the original data form by the necessary data processing, on the one hand, and the manufacturing of the given product of the three-dimensional representation as a three-dimensional object, on the other hand. Because of its dual utilization capability, the device is therefore especially suited for the visualization and development of such three-dimensional products and avoids time-consuming transformations and the use of different devices in the development process for such products.

The invention characterized incorporates a substrate carrier device that serves for use both with the manufacturing of three-dimensional products in the first application mode and with two-dimensional printing in the second application mode. In particular, for this purpose the substrate carrier device can be designed to accommodate one or more substrate plates. Furthermore, it can also be designed for use itself as a substrate plate, for example by designing the substrate device as a transport device with a corresponding surface area for accommodating three-dimensional products. Here, we refer in particular to the transport devices described above, especially the conveyor designs. The substrate carrier device is furthermore designed for accommodating a print carrier, whereby such a connection is understood to mean that the print carrier is placed flush on top or against the device or can be fixed with friction locking and, in particular, the substrate carrier device is also designed to withdraw or transport a print carrier from a stack and move this to the region of the material application device.

The substrate carrier device itself can be moved in the direction of one or more axes in order to generate the relative movement to the material application device. In principle, this relative movement can be generated by a fixed partner (material application device or substrate carrier device) and a second partner with multi-axis movement (material application device or substrate carrier device). The invention also includes combined movement forms, with which both partners move along certain axes and, in particular, swiveling about certain axes is also possible in order to implement the movements required for the first and second application modes.

In accordance with a first preferred design form, the device characterized also allows the selective application of predetermined regions with a curable material in the first application mode and the application of color to the determined regions in the second application mode by means of a printing head capable of movement along at least one axis. According to this design, one or more printing heads are made available, each designed to selectively apply both the material for three-dimensional printing and color for a two-dimensional print to predetermined regions, the printing head being capable of movement along at least one axis in order to implement the relative movement required for selective application. In principle, several such printing heads can be positioned along a common axis or along parallel axes in order to enable a fast and efficient production process. Alternatively to this design, a design can be foreseen in which at least two printing heads are available and one of the two printing heads is designed for the application of the curable material and the other of the two printing heads for the application of color in the second application mode.

In particular, a first inlet opening, leading to a color lead channel and possibly to corresponding other color lead channel inlet openings for each additional color and a second inlet opening leading to a material lead channel for the curable liquid, can be made available, with the color lead channels and the material lead channels connected to a common discharge nozzle, preferably in a common lead channel leading to a discharge nozzle, or a first inlet opening leading to a color lead channel, possibly to corresponding additional color lead channels for each additional color and the material lead channel to separate discharge nozzles, preferably each color lead channel leading to separate discharge nozzles. These designs allow different enhancements of the device for dosing both the curable material for the first application mode and the color for the second application mode from the same printing head and discharging from this printing head. Accordingly, separate inlet and outlet openings and nozzles can be made available on the printing head, which are supplied via separate lead channels in the printing head with the curable material or the color. Alternatively, the channels can lead to the same nozzle in order to supply curable material or color, according to the application mode, but also possibly to discharge curable material mixed with color from this nozzle for manufacturing selectively dyed products. This design is especially advantageous for the selective dying of products by selective color mixing in the curable material. However, the same effects can be produced if controlled accordingly when the curable material and the color are discharged to the printing head by separate nozzles in order to manufacture selectively dyed products with the simultaneous or time-shifted application of color and curable material.

The printing head and the nozzles/discharge nozzles of the printing head can, in particular, incorporate an actuator in order to realize a bubble jet printer, piezo printer or discharge valve printer design for the discharge of the curable material and color(s). In principle, this is understood to mean that the material and color(s) are applied under pressure in order to discharge them from the printing head. This pressure can, for example, be generated in the vicinity of a material or color tank or in the vicinity of the printing head.

In accordance with another preferred design form, the control unit and the application device are characterized in that, in a third application mode, preferably each layer, material and one or more colors are applied to a region, in particular in such a way that material and one or more colors are mixed before or in the printing head and the mixture then applied or the material and the color(s) are applied simultaneously or time-shifted via separate nozzles and application is carried out in such a way that the material of the layer is applied in a predetermined color pattern or, in order to apply material and one or more colors to separate regions, in particular in such a way that material is applied from a first material application nozzle and one or more colors from one or more color application nozzles and application is carried out in such a way that the material of a previous layer or the material of the current layer is provided with a predefined color pattern. In addition to the direct manufacturing of three-dimensional products in a single color, in which the curable application material has its own color in the first application mode and the manufacturing of two-dimensional prints on a print carrier in the second application mode, the design of the device with this third application mode enables the manufacturing of individual three-dimensional products with selective dying in the third application mode, whereby the three-dimensional color printing of products can be carried out according to the instructions above.

In the preceding embodiment it is further preferred if one or a plurality of inlet openings leading into material flow channels are provided for dispensing one or a plurality of materials for building different material regions in the product or for curing of the plurality of materials in a chemical reaction with each other. With this embodiment the manufacturing of regions having different material properties in one product and the manufacturing of products from materials requiring two or more components for curing is achieved.

Another preferred design of the device according to the present invention incorporates a substrate plate stack and/or a print carrier stack interacting mechanically with the substrate plate carrier for the feeding of substrate plates or print carriers from the substrate plate stack or the print carrier stack, respectively. With this design, the efficient and cost-effective operation of the invention is possible. In particular, this design allows the optional and alternating production of products or prints and accesses the relevant stacks. This is understood to mean that the print carrier stack can be in the form of a paper stack of the design known from conventional printing. In accordance with the invention, such a print carrier stack and substrate plate stack can be made available in order to supply the first, second and, possibly, third application modes with the required consumable material. This is understood to mean that, in particular, a substrate plate stack is not necessary when the substrate carrier device is accordingly designed and a surface for forming the three-dimensional products and the follow-on separation of these products following manufacture is provided. Furthermore, it is understood that the substrate plates in the substrate plate stack can be designed as reusable plates, which are removed from the device following production in order to separate the product formed on these and, possibly after reconditioning, used again for the production of a new product.

In accordance with another preferred design form, the device according to the invention incorporates the substrate plate carrier as an endless conveyor device and the material application device is designed to discharge the curable material directly to the substrate plate carrier and/or a separating device is positioned on the substrate plate carrier to separate the manufactured product after production from the substrate plate carrier or a substrate plate positioned on this, whereby the endless conveyor device is preferably turned around and thus deformed by a deflecting device, enabling the separation of the products. Such a design enables a particularly efficient form of the device characterized, with reduced consumable materials, including an endless conveyor device in order to form the products and provide the axis of movement necessary for the relative movement. Furthermore, this design incorporates a separating device, whereby it is understood that this separating device can be implemented in the form of a processing device which actually performs the separation process by machining. Alternatively, however, the separating device can also be in the form of a mechanism that exerts a shear or bending force or another type of force on the connection plane of the product to the surface on which the product is formed in order to separate the product from the surface. In particular, the separating device can be implemented as the guide roller of a conveyor belt, causing a deformation of the conveyor belt to a curved plane, allowing the detachment of the product formed on the conveyor belt in the boundary layer between the product and the conveyor belt. The separating device may alternatively be designed as a heated separating element, in particular a blade, a wire or the like, the temperature of which may be controlled in open or closed loop control such that it is above melting or evaporating temperature of the material.

Another preferred design is characterized in that the curable material is discharged from a first nozzle arrangement with at least one nozzle and the color from a second nozzle arrangement with at least one nozzle and the first and second nozzle arrangements are positioned on a printing head moved along at least one axis during application, or the first nozzle arrangement is positioned on a first printing head and the second nozzle arrangement is positioned on a second printing head and the first and/or second printing head is moved along one axis during application, whereby the axes of the printing heads are parallel to each other, in particular coaxially, and/or the first and second nozzle arrangements are movable independently of each other during application. According to this design, the curable material and the color are discharged from separate nozzle arrangements, whereby it is understood that each nozzle arrangement can incorporate one or more nozzles. In certain preferred design forms, the nozzle arrangements can be allocated to one and the same printing head and consequently move together. In other preferred design forms the nozzle arrangements are allocated to separate printing heads and can therefore be moved independently of each other. In principle, it is understood that that the design forms referred to are suited to the implementation of the first and second application modes and, possibly, the third application mode for the manufacturing of a selectively dyed, three-dimensional product. In the sense of this description and the claims, a nozzle is understood to mean an outlet opening joined to a lead channel, with a diameter corresponding to or narrower than that of the lead channel.

Yet another preferred design form is characterized in that the substrate carrier device and the material application device can be moved in relation to each other and are guided by guide devices in such a way that the consecutive layers are applied in the first application mode in layer plates aligned obliquely to the surface of the substrate plate and the colors are applied in the second application mode, preferably in a layer plane corresponding to the first operating mode, in particular along an axis lying in such a plane, and the substrate plate or the print carrier, respectively, is moved in at least one direction during application, the direction having a directional component normal to the layer plane. With this design, a specific advantageous construction is made available for the relative movement between the material application device and the substrate carrier device, enabling the continuous production of three-dimensional products and two-dimensional prints. The device is characterized in that layer application is oblique to the surface of the substrate plate and substrate carrier device. This oblique arrangement of the device enables the manufacturing of products with extended lengths, and theoretically this arrangement allows the manufacturing of a product with infinite length. In accordance with the invention, this design form also allows the alternative working procedure in the second application mode, in particular in which the application device is moved obliquely along one axis and movement along a second axis is possible, in particular the transport of the printing medium along this second axis.

It is further preferred that the control device is designed to control the material application device in such a way that it dispenses material selectively on predetermined regions corresponding to the cross-section of a product in the respective layer.

The device according to the invention may be further improved by a control for controlling the material application device, the control being designed for controlling the material application device such that a dividing wall is manufactured during the manufacturing process of the product by curing of the applied material.

It is further preferred that the material application device is guided in such a way that it is slidably supported in a plane aligned oblique to the surface of the substrate plate.

The device according to the invention may be further improved by a second material application device being designed and movable for applying a second material as a homogeneous layer before a selective material application is carried out.

It is further preferred that the material application device is adapted to selectively apply a material mixture of two different materials, wherein the two different materials are adapted to cure with each other by chemical reaction after selective application, or selectively apply a material, wherein the material is adapted to cure after the selective application by chemical reaction with the environmental gas, or selectively apply a molten material, wherein the molten material is adapted to cure after selective application by cooling down.

It is further preferred that the material application device(s) is/are arranged and adapted with respect to the substrate plate and the direction of gravitation in operating position of the device in such a way that the material dispensed thereon is fed in gravitational direction as a layer on the substrate plate or layers dispensed thereon or on predetermined regions of the substrate plate, respectively, or layers arranged thereon.

It is further preferred that the control device is adapted to control the material application device and/or the conveyor device in such a way, that a layer with a thickness between 5 µm and 200 µm is applied.

With regard to the specific design forms and advantages of such a device for two-dimensional and three-dimensional printing, we refer to the above elaboration of the device corresponding to this form and the accordingly elaborated process for three-dimensional printing in such an oblique arrangement. Here, it is understood in principle that the device can be designed for two-dimensional and three-dimensional printing in such a way that the additive production process is possible with the first application mode and, possibly, in the third application mode follows and the device corresponds to that described above.

The object of the invention is satisfied according to another aspect of the invention by a process for the manufacturing of products with individual geometry, in particular dental prostheses or dental parts, in which the first application mode or the second application mode can be selected via an input interface and, in the first application mode at least a three-dimensional product can be manufactured at or on the surface of a substrate plate by means of an additive manufacturing process, with the steps applying a curable material in consecutive layers, selectively curing one or more predetermined regions during or after each layer application, and thereby joining these predetermined regions to the underlying layer, whereby the predetermined regions(s) is(are) predetermined based on cross-sectional geometry of the product in the respective layer and the curable material is applied in several consecutive layers for manufacturing the three-dimensional products, whereby in the second application mode one or more colors are applied to selected regions of a print carrier to produce single-colored or multi-colored prints.

The process can be characterized in that moving a printing head along at least one axis to access the regions selected for application and the printing head is designed for the discharging of curable material in the first application mode and one or more colors in the second application mode.

Furthermore, the process can be characterized in such a way that one color enters through a first inlet opening into a color lead channel in the printing head and each additional color, respectively, through another color lead channel into the printing head and the curable material enters through a second inlet opening into a material lead channel, and that the color lead channel(s) and the material lead channel lead into a common discharge nozzle preferably into a common lead channel leading into a discharge nozzle, or one color enters through a first inlet opening into a color lead channel in the printing head and each additional color, respectively, through a corresponding inlet opening into a color lead channel in the printing head and the curable liquid enters through a second inlet opening into a material lead channel, with the material lead channel leading to separate discharge nozzles, preferably each color lead channel to separate discharge nozzles.

Further, the process can be characterized in such a way that a third application mode in one, preferably in each layer, material and one or more colors are simultaneously applied to a region, in particular by mixing the material and one or more colors in the printing head and then applying the mixture in such a way that the material of the layer is applied in a predetermined color pattern or the material and one or more colors are applied to separate regions, in particular by applying material from a first material application nozzle and one or more colors from one or more color application nozzles in such a way that the material of a previously applied layer or the material of the layer is provided with a predetermined color pattern.

Thereby it is particularly preferred that a plurality of materials is applied, preferably from a plurality of material dispensing nozzles, and that the three-dimensional product cures by chemical reaction of the plurality of materials with each other or that the three-dimensional product includes regions having different mechanical material properties.

Furthermore, the process can be characterized in that the substrate plate is transported from a substrate plate stack and/or the print printing carrier from a printing carrier stack.

The process can be further characterized in that the substrate plate is designed as an endless conveyor device and the products manufactured on the device are detached after production from the substrate plate by a separating device, in particular by turning around and thereby deforming the substrate plate in order to detach the products.

The process can be further characterized in that discharging the curable material from a first nozzle arrangement with at least one nozzle and the color from at least a second nozzle arrangement with at least one nozzle, the first and second nozzle arrangements being positioned a printing head which is moved along at least one axis during application, with the first nozzle arrangement positioned on a first printing head and the second nozzle arrangement on a second printing head moved along one axis, whereby the axes of the printing heads are parallel to each other, in particular running coaxially, and/or the first and second nozzle arrangements are moved independently of each other during application.

The process can be further characterized in that it enables application to the consecutive layers in the first application mode, aligned obliquely to the surface of the substrate plate, and the color in a second application mode is preferably applied in a layer plane corresponding to the first operating mode, in particular along an axis lying in such a plane, and the substrate plate or the printing carrier, respectively, is moved in at least one direction during the application process, the direction having a directional component normal to the layer plane.

The process can be further extended to incorporate the additive manufacturing process in the first application mode in accordance with the dependent claims.

With regard to the specific advantages, design forms and variants of such a process, we refer to the above elaboration of the device corresponding to this form and the accordingly elaborated device.

III.3 Third Embodiment: Apparatus and Method for an Additive Manufacturing Method on a Plurality of Substrate Plate Segments The object of the invention is satisfied by a further aspect of the invention by a device for the manufacturing of products with individual geometry, comprising a substrate carrier device and a material application device above the substrate plate, whereby the substrate plate is subdivided into several detachable substrate plate segments joined to each other or to a base carrier.

The proposed device is characterized in that a material application device, with which a material layer can be applied to all substrate plate segments of the substrate plate in one operating cycle and/or a signal control unit is coupled to the material application device in order to control the material application in such a way that the material is selectively applied to predetermined regions corresponding to the cross-section of a product in the respective layer, is positioned above a substrate plate. In particular, this can be a material application device that is movable in relation to the substrate plate, preferably a material application device positioned above the substrate plate.

Furthermore, a radiation source can be installed above the substrate plate. The material application device and radiation source are controlled by a production control unit in such a way that the material layer applied in the first operating cycle is either selectively applied to predetermined regions and cured there or, possibly, cured in another operating cycle by the radiation source or another means, for example by the addition of another material to predetermined regions of the layer for selective curing.

The invention can be characterized in that the substrate plate is subdivided into several segments. The segments can be detachable and joined to each other, by which it is understood that one segment, respectively, is joined to only one adjacent segment or one segment can be joined to several adjacent segments. Alternatively, it is also possible for the segments to be positioned next to each other, each segment being detachably joined to a base carrier. With the device described, in this way it is possible to generatively manufacture several products distributed over several substrate plate segments and adjust the heights of the substrate segments in relation to each other in such a way that the products can be produced in different stages of manufacturing on different substrate plate segments or that the products manufactured on a first substrate plate segment are removed with the substrate plate segment and detached from this before one or more products are removed from another substrate plate segment and detached from this segment.

The device can be characterized in that it incorporates a radiation source for a high-energy beam and collimation to direct the beam to predetermined regions of the material layer on the substrate plate.

The device described can be characterized in that the material application device is adapted for the simultaneous application of a material layer above a certain number of substrate plate segments in one operating cycle.

Furthermore, the device described can be characterized in that the substrate plate segments and the material application device are movable in relation to each other by means of one or more actuators in such a way that the clearance between the surface plane of a first substrate plate segment and a layer region of the material layer applied to it for the manufacturing of a first product differs from the clearance between the surface layer of another substrate plate segment and a layer region of the material layer applied to it for manufacturing the other product.

Furthermore, the device can be characterized in that a material separating device, in particular a material suction device, whereby the material separating device is adapted to detach non-cured material from the peripheral region of a manufactured product, the material separating device being preferably arranged in such a way that it can leave the material intact on another substrate plate segment adjacent to this.

Another preferred design form is characterized in that the device is equipped with a control unit for the collimation of the high-energy beam, which is adapted to drive the collimation or the material application device in such a way that, in the first phase of manufacturing, only predetermined regions of a layer are selectively cured which serve for the manufacturing of a first product on a first substrate plate segment and, in a last phase of manufacturing, only layer regions are selectively cured which serve for the manufacturing of another product on another substrate plate segment, and in a phase between the first and last phases of the manufacturing process a layer is cured which serves for the manufacturing of the first and the other product.

The device can also be characterized in that a control unit for controlling the material application device and/or driving at least one actuator for the relative movement between the substrate plate segments and the material application device, which is adapted to provide a resulting height of the material bed following the application of all material layers on a first substrate plate segment that is different from the resulting height of the material bed following the application of all material layers on another substrate plate segment. In this way, products of different structural heights can be manufactured simultaneously on different substrate plate segments.

Furthermore, a preferred design is characterized in that a processing device on the material application device for the stripping of a part of the surface of the cured material regions, preferably for grinding the surface of the cured material regions, is allocated to a previously applied material layer.

Furthermore, a preferred design is characterized in that the substrate plate segments are positioned on an endless conveyor belt that runs partly or entirely in a processing chamber and that is sealed against the surroundings to the extent that a controlled, in particular an inert, atmosphere can be realized.

Another design form is characterized in that the device has at least one lifting direction coupled to or capable of coupling to each substrate plate segment in order to raise or lower the respective substrate plate segment in the vertical direction independently of the other substrate plate segments during the manufacturing process.

Furthermore, the device is characterized in that a single radiation source, in particular in the center of a single radiation beam, is utilized for the curing of the products manufactured on all substrate plate segments.

Furthermore, the device is characterized in that a dividing wall between the substrate plate segments, separating the formation space above the substrate plate segment from the formation space above an adjacent substrate plate segment.

Furthermore, a preferred design is characterized in that the dividing wall between two substrate plate segments is joined to at least one of the two substrate plate segments or sealed off from this substrate plate segment in such a way that no material can pass between the dividing wall and the substrate plate segment.

In accordance with another preferred design form the device is characterized by a control unit for controlling the material application device or the collimation device of the high-energy beam, the control unit being designed for controlling the material application device or the collimation device so that the dividing wall is created during the manufacturing process by the selective application or selective curing of the applied material.

Finally, the device described can be characterized in that it incorporates a control unit for controlling the high-energy beam and/or the material application device, designed to position the high-energy beam and/or the material application device over the nth material layer according to the control data, which is defined according to the geometrical data of an xth cross-sectional area of a first product, in order to cure parts of the nth material layer by means of the high-energy beam or selective material application, respectively, position the high-energy beam and/or the material application device over the (n+1)th material layer according to the control data, which is defined according to the geometrical data of an (x+1)th cross-sectional area of the first product, in order to cure parts of the (n+1)th material layer by means of the high-energy beam or selective material application, respectively, position the high-energy beam and/or the material application device over the nth material layer according to the control data, which is defined according to the geometrical data of a yth cross-sectional area of a second product, in order to cure parts of the nth material layer by means of the high-energy beam or selective material application, respectively, and position the high-energy beam and/or the material application device over the (n+1)th material layer according to the control data, which is defined according to the (y+1)th cross-sectional area of the second product, in order to cure parts of the (n+1)th material layer by means of the high-energy beam or selective material application, respectively, where x and y are not identical.

The device described works preferably according to a process with the steps: providing of a substrate plate, which is subdivided into a first substrate plate segment and at least one other detachable substrate plate segment, joined to each other or to a base carrier, manufacturing of a first product on the first substrate plate segment by the consecutive application of material layers to the first substrate plate segment, and, following material application, selective curing of the predetermined regions on each material layer applied, manufacturing of at least one other product, applied to at least one other substrate plate segment by the consecutive application of material layers to the other substrate plate segment, and, following material application, selective curing of the predetermined regions on each material layer applied.

In particular, this can be characterized in that the process takes place according to the following steps: manufacturing of one or more products on or at the surface of a substrate plate by selective curing, in particular by selective sintering or melting, according to which the material is applied in consecutive layers, one or more predetermined regions are cured following each material application, and joining to one or more regions of the adjacent, in particular the underlying, layer, whereby the predetermined regions are defined on the basis of the cross-sectional geometry of the product in the respective layer, selective application of the material in the predetermined regions of the layer, and the providing of a substrate plate, which is subdivided into a first substrate plate segment and at least one other detachable substrate plate segment, joined to each other or to a base carrier, manufacturing of a first product on the first substrate plate segment by the consecutive application of material layers to the first substrate plate segment, and, following material application, selective curing of the predetermined regions on each material layer applied, manufacturing of at least one other product, applied to at least one other substrate plate segment by the consecutive application of material layers to the other substrate plate segment, and, following material application, selective curing of the predetermined regions on each material layer applied. With this design, selective curing takes place following material application and is restricted to predetermined regions as a result of selective material application.

The process is characterized in that a substrate plate is provided on which a first and another product are generatively manufactured simultaneously in a first and another corresponding substrate segment and these detachable substrate segments are joined to each other or to a base plate. This allows the removal of a single substrate plate segment following manufacturing of the product formed on this segment in order to separate the product from the substrate plate segment, while another product is still being generatively manufactured on another substrate plate segment.

In particular, with this process material layers can be applied to at least two substrate plate segments, with at least one of the material layers spread over both substrate plate segments. In this case, the process can take place in such a way that, initially, one material layer can be applied to at least two substrate plate segments and this material layer selectively cured in the region above both substrate plate segments.

In particular, the substrate plate segments can interact with a single material application device in such a way that one product is formed on one substrate plate segment in a first stage of manufacturing, for example with an nth layer above the substrate plate, and another product in another stage of manufacturing can be formed on another substrate plate segment, for example with an mth layer formed above the substrate plate, where m and n are not identical and the nth and mth layers are applied by the material application device in one operating cycle.

With this process, time-shifted production start times for manufacturing several products on a substrate plate are possible, whereby the products are partly manufactured simultaneously and also separated time-shifted from the substrate plate. In this way, it is possible to utilize the substrate plate to achieve high productivity for the production of several products and, at the same time, avoid having to start production only after all production data for all products to be manufactured on the substrate plate are available. Instead, the start of production can be individually defined for each substrate plate segment and, accordingly, the end of production can also be individually defined for each substrate plate segment. In this way, the duration of production for an individual product can be considerably reduced.

In principle, it is understood that the substrate plate can be subdivided into two, three or more substrate plate segments. In particular, this is understood to mean the actual physical subdivision into separate components that can be accordingly joined to a substrate plate. In principle, it is possible to apply material to all substrate plate segments with a single common material application device, as is preferred because of the resulting production efficiency. For certain applications, however, it can be advantageous to apply material to the substrate plate segments by means of separate material application devices, whereby here again it is understood that, with the process described, while time-shifted start of production start and, accordingly, time-shifted end of production of the products on the different substrate plate segments takes place, on several substrate plate segments simultaneous production preferably takes place with the simultaneous application of material to all substrate plate segments and the follow-on selective curing of predetermined regions for the generative manufacturing of products in order to achieve high productivity.

A first preferred process form is characterized in that one of the several predetermined regions is selectively cured by means of a high-energy beam and joined to one or more regions of the underlying layer. This curing effect can be utilized in addition to another curing effect or alone as a curing mechanism. In principle, curing by means of a high-energy beam is understood to mean the process of curing a previously applied material by a high-energy beam, for example by photopolymerization, or in which a material previously applied as a free-flowing powder, granulate, etc. is heated by irradiation and therefore partly or completely melted, and then solidified or sintered by cooling. In particular, this curing accompanies the joining of the material region subjected to radiation to an adjacent or underlying material region, in order to form the product as an integral component.

Furthermore, a preferred process form is characterized in that the substrate plate segments are provided next to each other in such a way that no material can enter. In particular, for this purpose a corresponding seal is provided between the different substrate plate segments or the substrate plate segments are joined in such a way that material cannot pass between the substrate plate segments.

Furthermore, the process is characterized in that the substrate plate segments are designed as segments of an endless conveyor device. This design enables the particularly efficient continuous generative manufacturing of products. The substrate plate segments can, for example, be attached to an endless conveyor belt or joined to each other in such a way that form such an endless conveyor belt in the form of a link chain. In this case, the substrate plate segments can be moved successively along an upper run and a lower run, whereby layer application and selective curing take place during movement along the upper run. The removal of non-cured material applied from the interstitial space between the products manufactured and the removal of the products can also take place in the upper run region, for example by corresponding suction devices or mechanical separating devices. At the same time, however, it is also possible to allow the separation of the non-cured material in the upper run region to take place by itself, for example by gravity, and the finished products can be removed either together with a substrate plate segment or directly from the substrate plate segment in the upper run.

Furthermore, a preferred process form is characterized in that the substrate plates are designed and positioned in such a way that the first product or a group of first products is formed on a single substrate plate segment and the other product or group of other products is formed on one or more substrate plate segments. With this design, on the one hand one or more products can be manufactured on a single substrate plate segment and in this way manufacture small products with very fast production time. On the other hand, it is also possible to manufacture a single product on several substrate plate segments. In particular, this can be advantageous when larger products are to be manufactured with the process described that is products for which the longitudinal dimension or contact area is larger than the surface of a substrate plate segment. Furthermore, this is characterized by the possibility to manufacture a group of several products on two or more substrate plate segments. In particular, this may be necessary for products that are especially long in only one particular direction. Thus, with the process described it is possible to manufacture a product having a length extending over several substrate plate segments. When several such products are to be manufactured, in accordance with this design form a group of such products can be formed and this group extended over several substrate plate segments.

Furthermore, a preferred form is characterized in that the material is applied in a first manufacturing stage in a quasi-continuous process to the substrate plate and selected predetermined stages of each layer applied are cured and, in a second manufacturing stage, the finished cured products are removed quasi-continuously. This production method enables high-quality generative manufacturing in a first manufacturing stage and, at the same time, the removal of the finished products in a second manufacturing stage that is separate from the first manufacturing stage with no negative effects of generative production. In particular, this can be achieved in that the substrate plate segments are attached to an endless conveyor belt or the substrate plate segments form such a conveyor belt and the substrate plate segments are accordingly transported from the first manufacturing stage to the second manufacturing stage. In particular, with this design the first manufacturing stage can be held in a closed, controlled, in particular an inert gas, atmosphere in order to satisfy the necessary marginal conditions for certain processes, while the products in the second manufacturing stage are ejected, the second manufacturing stage includes an air lock, or the products are already ejected from the controlled atmosphere during transport from the first manufacturing stage to the second manufacturing stage.

Furthermore, a preferred form is characterized in that, in a first process step, a material layer is applied above at least two, preferably more, substrate segments and, in a second process step, the material layer is selectively cured and that the maximum clearance between the first substrate plate segment and the layer applied to this segment for manufacturing the first product in at least one, preferably several, in particular all process stages, differs from the maximum clearance between the other substrate plate segment and the layer applied to this segment for manufacturing the other product. This form is understood to mean that a process stage incorporates the sequence of material application and selective curing and is therefore carried out repeatedly, whereby consecutive process stages exist in each process phase, in which material is applied to at least two, in particular several or all, substrate plate segments and these are then selectively cured in order to generatively produce several products on the several corresponding substrate plate segments. In accordance with the invention, this is characterized in that the layers on the substrate plate segments are applied in such a way that the clearance between the respective applied layer and substrate plate segment is different for at least two, in particular for each substrate plate segment. This clearance can differ in only one of several consecutive process stages, each of which consists of the sequence of material application and selective curing, in particular however the clearance can differ in all process stages, that is typically the sum of the applied layers above another substrate plate segment is, for example because the combined material application can only start at a point in time when one or more layers have already been applied to the two substrate plate segments. The process can, for example, be implemented in such a way that the heights of the different substrate plate segments can be individually defined in order to be able to apply one layer to all substrate plate segments in a common plane, regardless of whether the clearance of this layer in relation to the substrate plate segments is different for each substrate plate segment or in that the material application device is moved vertically during the material application process.

Furthermore, a preferred form is characterized in that the steps removing the non-cured material allocated to the first substrate plate segment without removing material from another substrate plate segment and the follow-on removal of the non-cured material allocated to the other substrate plate segment. For the quasi-continuous generative manufacturing process described, it is especially advantageous at the removal position for the removal of the non-cured material in this way that an adjacent region is not affected and that non-cured material remains in this adjacent region. During the generative manufacturing process the non-cured material has a supportive function and serves to take up and bear the overlying layers. As a rule, the non-cured material may therefore not be removed before the product is completely formed and cured. However, in order to avoid the requirement that the finished products must first move over a longer path to the removal position in order to guarantee process reliability it is advantageous when the material separating device can execute material removal without affecting the immediately adjacent substrate plate segment. The quasi-continuous production described makes this possible and avoids the need to provide a safety clearance between the material application device and the material separating device.

Furthermore, a preferred form is characterized in that, in a first phase of the manufacturing process only those layer regions are selectively cured which serve for the manufacturing of the first product and, in a last phase of the manufacturing process, only those layer regions are selectively cured which serve for the manufacturing of the other product and preferably in an intermediate phase between the first and last phases of the manufacturing process only those layer regions which serve for the manufacturing of the first and the other products. The quasi-continuous and simultaneous production of products described enables a fast and productive process for the individual manufacturing of small products.

Another preferred process form is characterized in that a dividing wall is provided between the substrate segments in order to separate the formation space above each substrate plate segment from the formation space above an adjacent substrate plate segment. Such a dividing wall enables or simplifies the removal of non-cured material above a substrate plate segment without affecting the non-cured material in an adjacent substrate plate segment. This is understood to mean that such a dividing wall can be made available as a component of the production device and in this case, for example, can be implemented so that it is simultaneously repositioned for material application in order to provide an exact height or somewhat less than this height, corresponding to the upper layer surface of the material applied in the region between two substrate plate segments.

In particular, this can be characterized in that the dividing wall is created by the curing of the applied material during the manufacturing process for the product. With this design, such a dividing wall is created from the applied material at the edge of each substrate plate segment during the manufacturing process. This process has the advantage that that elaborate dividing wall constructions are not necessary. Instead, a corresponding dividing wall is formed along the peripheral area of a substrate plate segment, which becomes higher with each layer applied and, in this way, reaches the overall height of the material layer bed. The dividing wall can be removed from the substrate plate segment during the removal of the products or in the course of removing the non-cured material from the adjacent substrate plate segments.

The two process forms above can be further characterized in that the dividing wall between two substrate plate segments is joined to at least one of the two substrate plate segments. At the same time, joining the dividing wall to the two substrate plate segments that it separates also provides sealing against the passage of material between the substrate plate segments. Here, the connection can be achieved by the generative formation of the dividing wall on one or both substrate plate segments or by a corresponding structural connection of a dividing wall component as part of the device.

Another preferred process form is characterized in that each substrate plate segment is individually moved in relation to the material application device in such a way that the clearance normal to the surface of the substrate plate and the layer applied by the material application device varies and the resulting height of the material bed on one substrate plate segment differs from the height of the material bed on another substrate plate segment. In accordance with this form, each substrate plate form can be individually moved to a different height, for example by means of an actuator that alternately accesses the substrate plate segments or several actuators, each allocated to a different substrate plate segment. This enables the positioning of the substrate plate segments to different heights, in order to apply the material layer in a single plane above the substrate plate segments. This material layer is then at different individual distances from the respective substrate plate segments that is in particular different individual distances to the plane of the surface of the respective substrate plate segment to which the first material layer has been applied. The form described is suited for the generative manufacturing of one product in a first manufacturing region on a first substrate plate segment and another product in another stage of production with material application common to both substrate plate segments, with accordingly more products in different manufacturing stages.

Furthermore, the process is characterized in that the cured region of the previously applied layer is ground before each application of material. Such surface treatment, which in particular can be in the form of grinding, but also as another machined process with geometrically defined or geometrically undefined cuts, will further improve the geometrical precision of the generative manufacturing process. In particular, such machining provides a defined contact surface and joining position for the overlying layer and the regions to be cured therein. In addition, the machining provides a defined layer thickness, which is advantageous for the reproducible geometric characteristics of the finished product.

Furthermore, the process is characterized in that, for the curing of the first and at least one other product, in particular all other products, a single beam from a single radiation source is utilized. In principle it is understood that, for the acceleration of the manufacturing process, several radiation sources or several beams from a single radiation source can be utilized. The manufacturing process described is, however, in particular characterized in that, while several products can be simultaneously manufactured with these products in different stages of manufacturing that is in particular formed from different numbers of layers. However, a special feature is that both the application of a layer by a single material application device for all substrate plate segments and products formed on top of these can take place and that, furthermore, the curing of the predetermined regions of a layer can take place by means of a single radiation source for all products to be manufactured.

Another preferred process form is characterized in that each substrate plate segment can be raised and lowered by a lifting device in the vertical direction during the manufacturing process, with raising lowering movements of the substrate plate segments independent of each other. In particular, the independent raising and lowering movements can be performed by means of an actuator that alternately accesses the substrate plate segments or several actuators, each allocated to a different substrate plate segment.

Furthermore, the process is characterized in that the material is applied to several substrate plate segments by the material application device in one operational cycle. This adaptation enables an efficiently functioning material application device and, at the same time, the individual manufacturing progress of the respective products manufactured on the several different substrate plate segments.

Finally the process can be further developed via the steps: selective applying of an n-th material layer or applying of a n-th material layer on a substrate carrier plate and selective curing of parts of the material layer by the effect of high energy radiation, especially laser radiation, on these parts of the material layer, directing high-power radiation or a material application device, respectively, across the n-th material layer in accordance with guiding data collected from geometric data of a x-th cross-section surface of a first product, selective material application or application of a n+1-th material layer on the n-th material layer, guiding of a high-energy radiation or a material application device, respectively, across the n+1-th material layer in accordance with guiding data determined from the geometric data of a x+1-th cross-section surface of the first product, guiding of a high-energy radiation or a material application device, respectively, across the n-th material layer in accordance with guiding data determined from the geometric data of y-th cross-section area of a second product, and guiding of high-energy radiation or a material application device, respectively, across the n+1-th material layer in accordance with guiding data determined from geometric data of a y+1-th cross-section area of the second product, whereby x is not equal to y. In this continuing form at least two products are produced by way of these being subjected to selective curing in two different layer sections of one and the same layer, whereby in this layer the products themselves have different heights displayed compared to the substrate plate.

The device and the process in accordance with the invention in line with the aspects described in this description are suitable in favorable manner for various applications in accordance with the invention. On the one hand, personalized products for consumer application can be produced using the device/process, for example the device/process can be supplied with a control which enables personal creation of figures, toy elements and similar items. Appropriately the invented device/process can also be used to produce individualized jewelry.

Another application for the device/process in accordance with the invention is the production of boards for printed circuits, especially for use, which in addition to the card cage attached conductor paths are produced, and this is achieved via appropriate generative production with the various materials required. In this context it can in particular be seen that using this device and process in accordance with the invention, two different materials can be processed simultaneously or time-delayed to produce a product made of two or more different materials. For this purpose the idea in accordance with the invention is developed so that an initial curable material is used for layer formation in a first process step and a second curable material, different to the first material, is used for layer formation in the same or subsequent layer in a second process step. This means that the application method of the device/process described above can also be enhanced with the possibility of applying a curable material and color application, and in terms of its design and development can be used with the option of application of a second curable material in place of or in addition to a color.

Other application options for the devices/process according to the invention include the production of individually formed foodstuffs in smaller and larger series. The invention is suitable for the production of food of meat products, dough for pastries, of vegetable or fruit products or confectionery, such as for example chocolate which is suitable for processing as curable material and which provides the user with a creative favorable form in terms of surface/volume ratios for processing and flavor effect.

Other applications in accordance with the invention for the devices and processes according to the invention include medical technology. Devices/processes according to the invention can be used for the production of artificial organs and organ structures for reproduction of such organs using a bio-technical method, and in the same way for the production of individually formed implants, orthotics and prostheses and similar items. This method of application is especially useful for the option of targeted production of individually formed and individually colored three-dimensional products, if aesthetically relevant components are involved. As such there is also a beneficial field of use for devices and process in accordance with the invention in the field of dental technology, especially in the use of the devices/processes for the production of dental prostheses and dental aids, moulds for the execution of dental or orthodontic intervention. In general the device/process according to the invention can be beneficially used to make models, moulds, guiding devices and similar items in an individual manner in a way so as to enable surgical intervention in the course of operative treatment in a safe manner with extreme precision compared to previous methods using standardized moulds/guiding devices.

Finally, beneficial use of the device/process according to the invention can also be found in the production of individual models for the visualization of products, structural situations in displays reduced or enlarged true to scale or as real 1:1 prototype model, for example in the field of town planning or architecture.

With reference to the aspects of the invention and embodiments as described in the foregoing and following description and the claims it is to be understood that the embodiments of the apparatus and the method for conducting an additive manufacturing process with oblique layer application, the conducting of an additive manufacturing process and a two-dimensional print process as well as the conducting of an additive manufacturing process on a plurality of substrate plate segments may be combined with each other, for example as an oblique layer application or a layer application on a plurality of substrate plate segments is conducted in a first application mode according to an additive manufacturing process in an apparatus which may alternatively allow a two-dimensional print process in a second application mode. In the same way single or a plurality of characteristics of specific preferred embodiments of these aspects may be combined with each other for another preferred embodiment.

IV. SHORT DESCRIPTION OF THE FIGURES

Figure 1B:
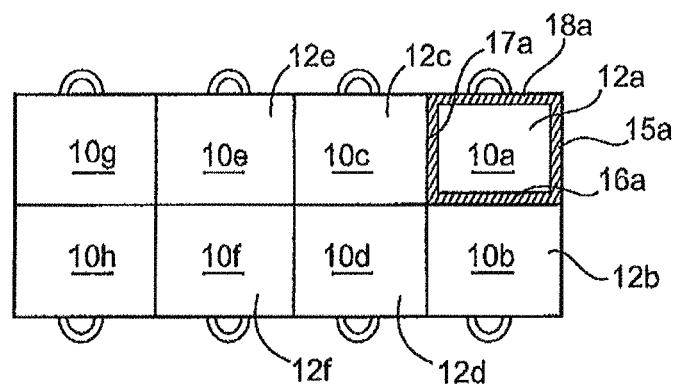
Figure 2:
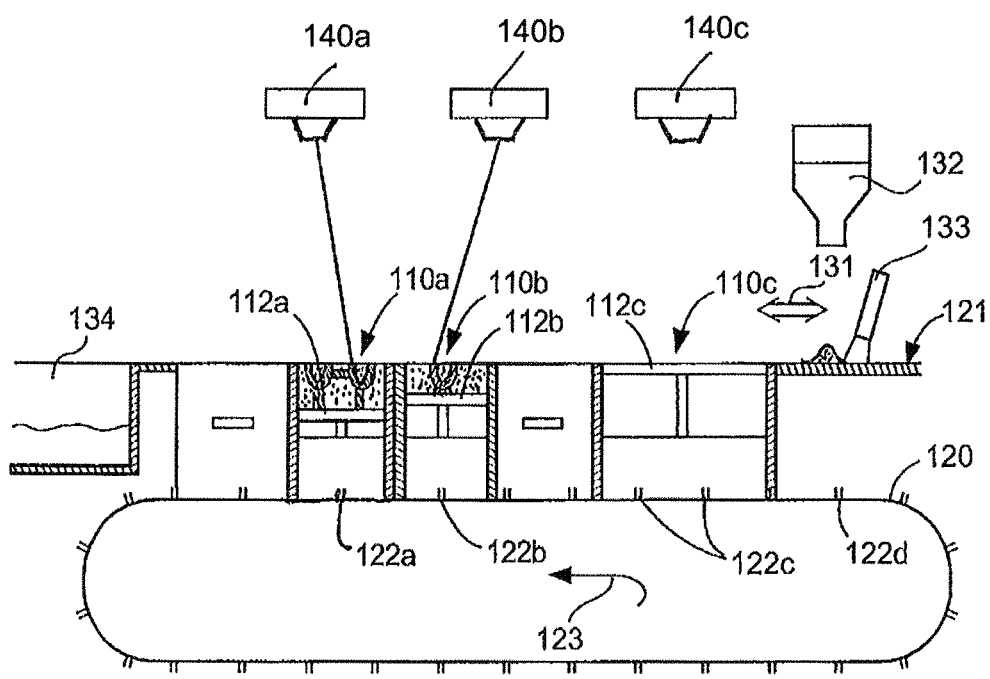
Figure 3:
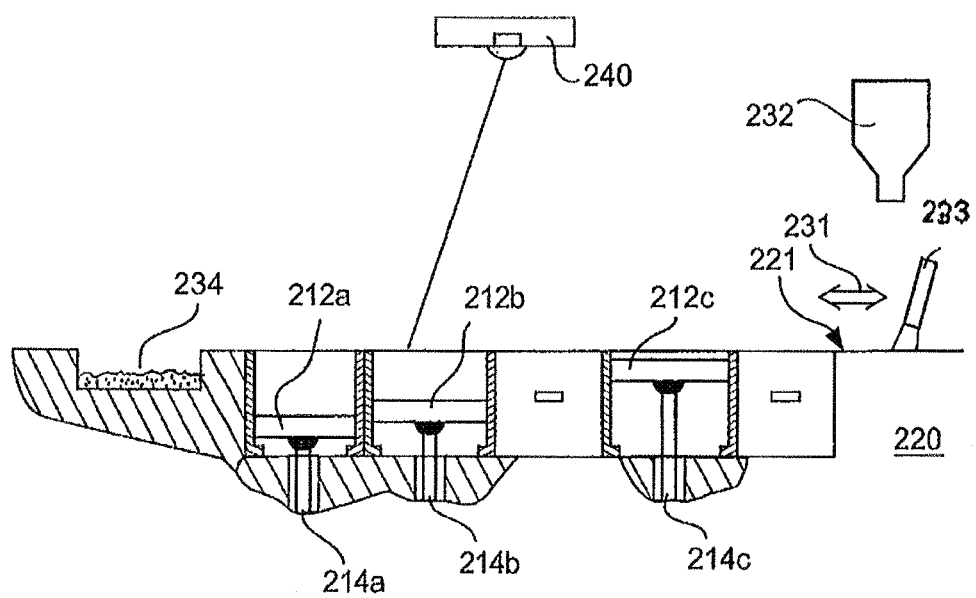
Figure 4:
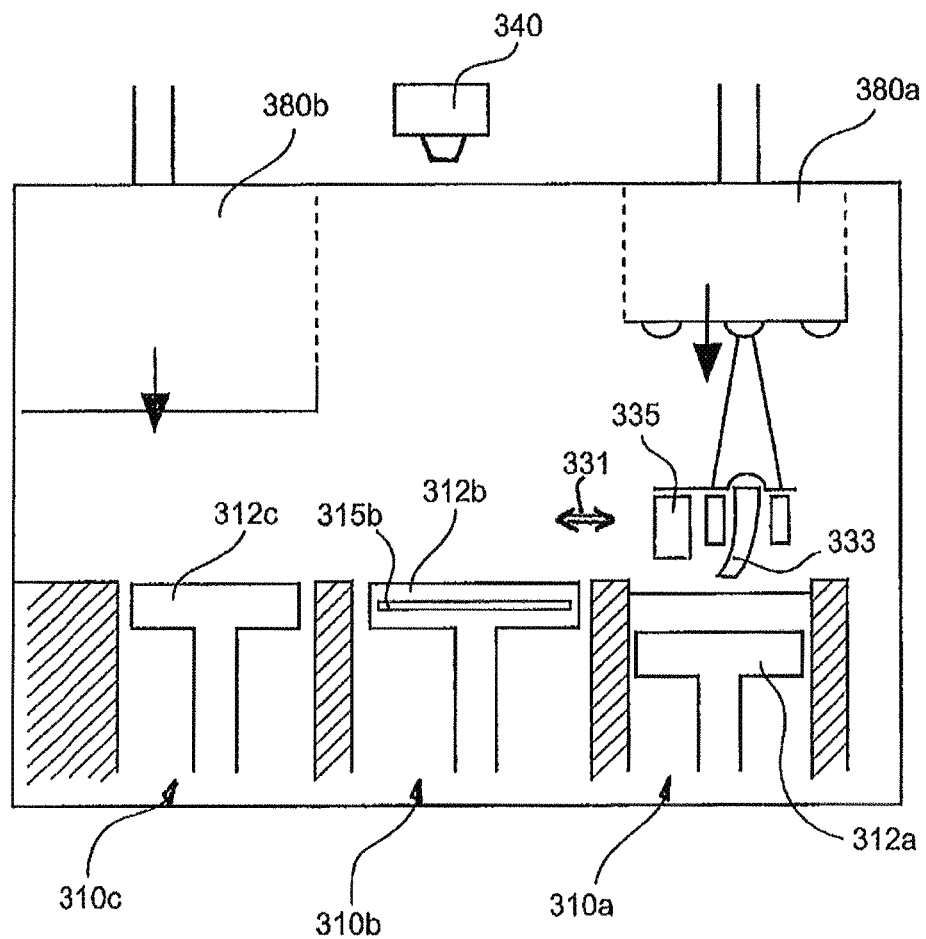
Figure 5:
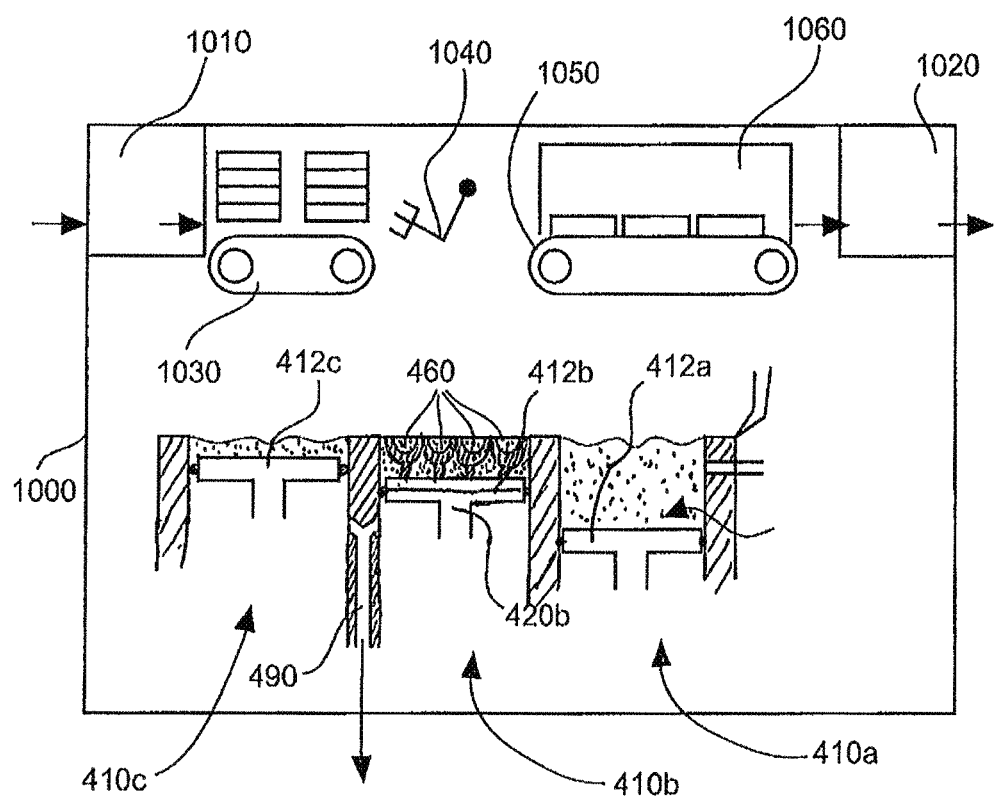

Preferred embodiments of the invention are described based on the figures (pieces) enclosed: These show:

FIG. 1A a diagrammatic, lengthwise side view of a first embodiment of the invention, FIG. 1B a top view of the embodiment pursuant to FIG. 1A, FIG. 2 a diagrammatic, lengthwise side view of a second embodiment of the invention, FIG. 3 a diagrammatic, lengthwise side view of a third embodiment of the invention, FIG. 4 a diagrammatic, lengthwise side view of a fourth embodiment of the invention, FIG. 5 a diagrammatic view of a production layout in accordance with a fifth embodiment of the invention, and.

Figure 6:
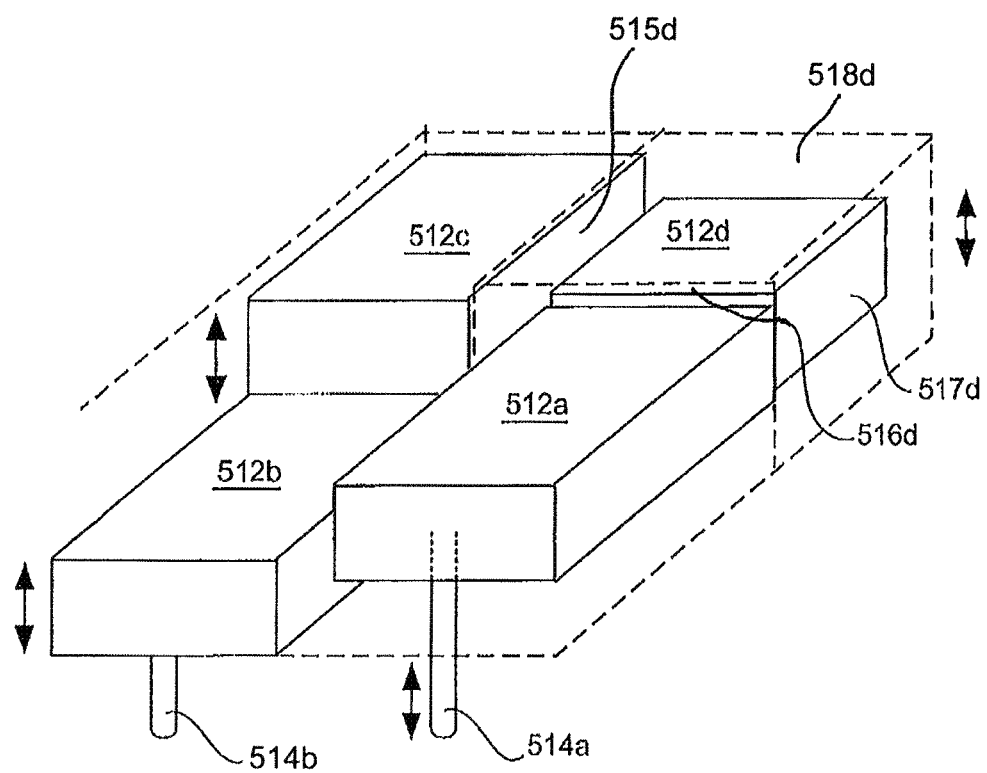
Figure 7:
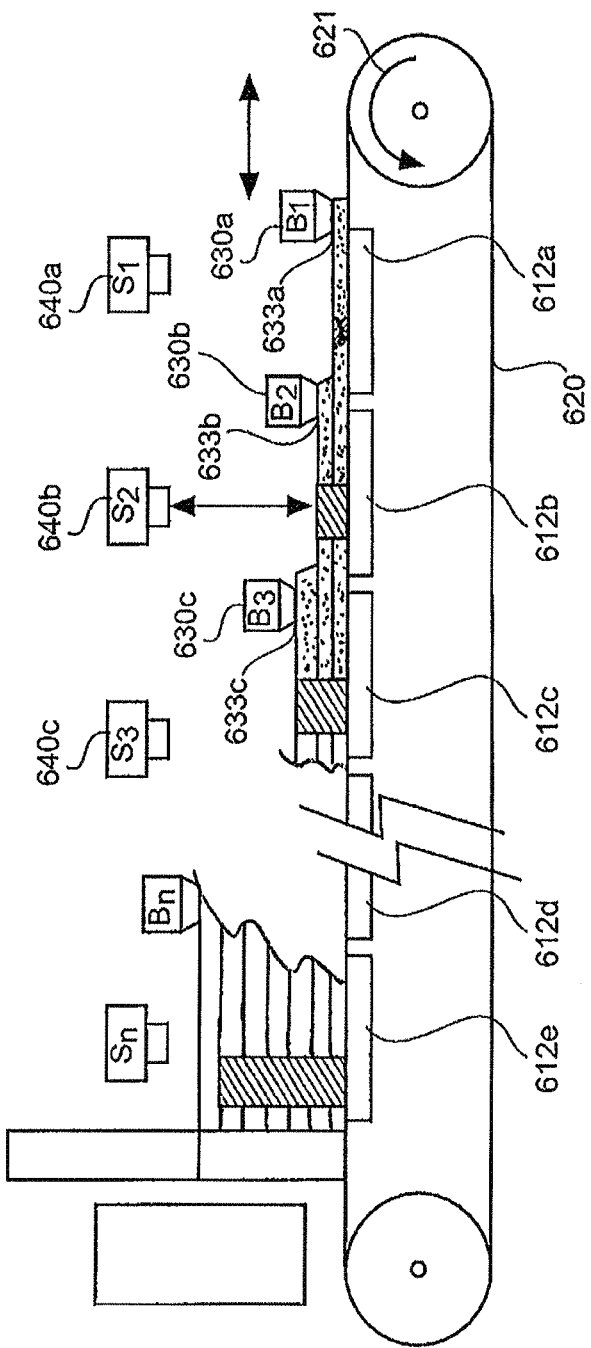
Figure 8:
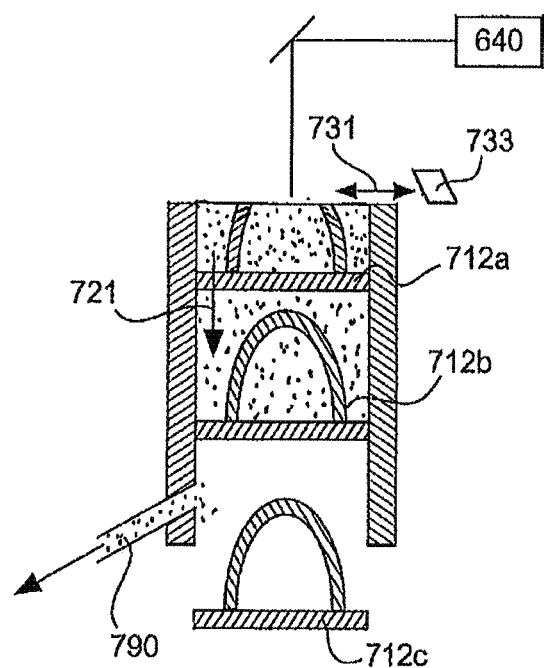
Figure 9:
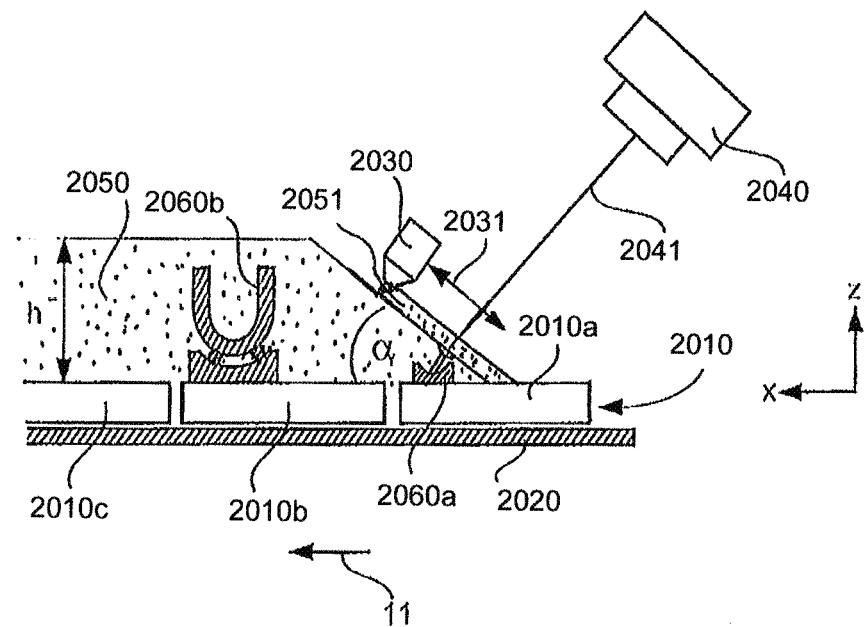
Figure 10:
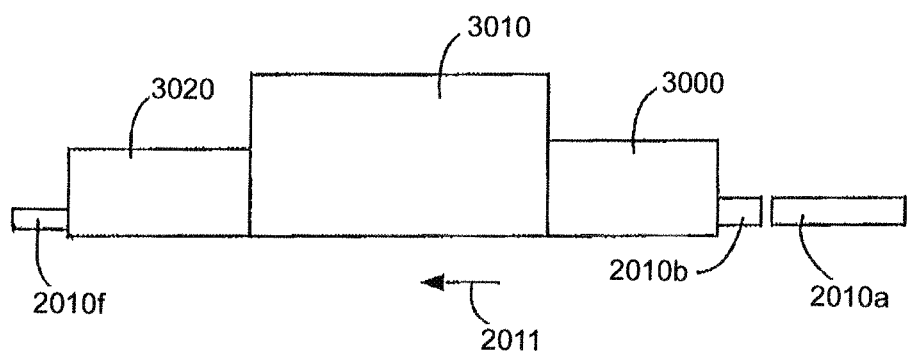
Figure 11:
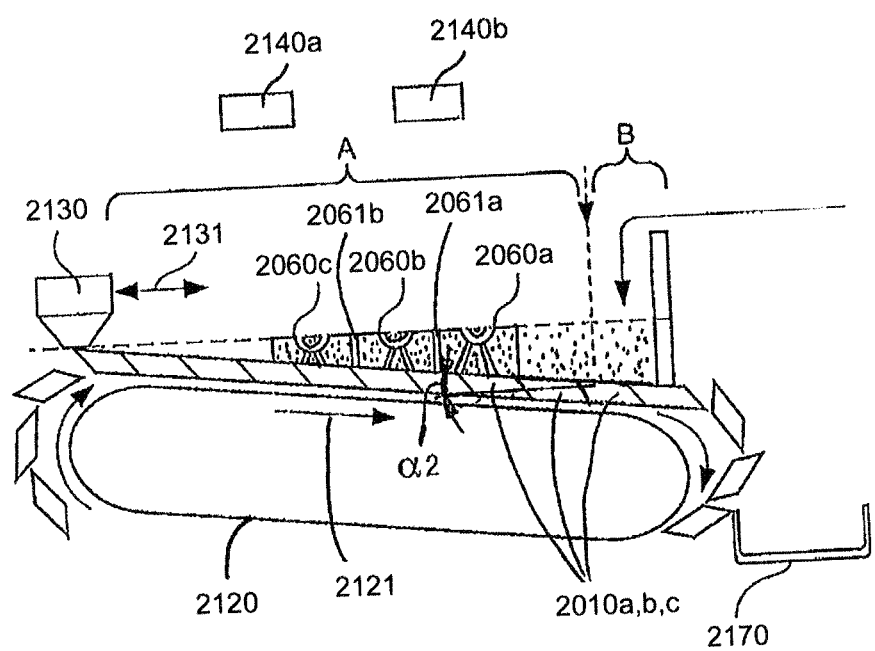
Figure 12:
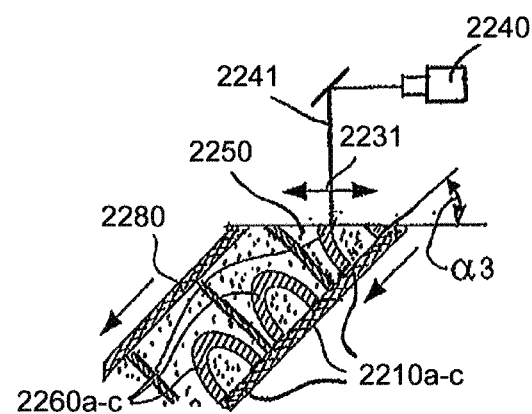
Figure 13:
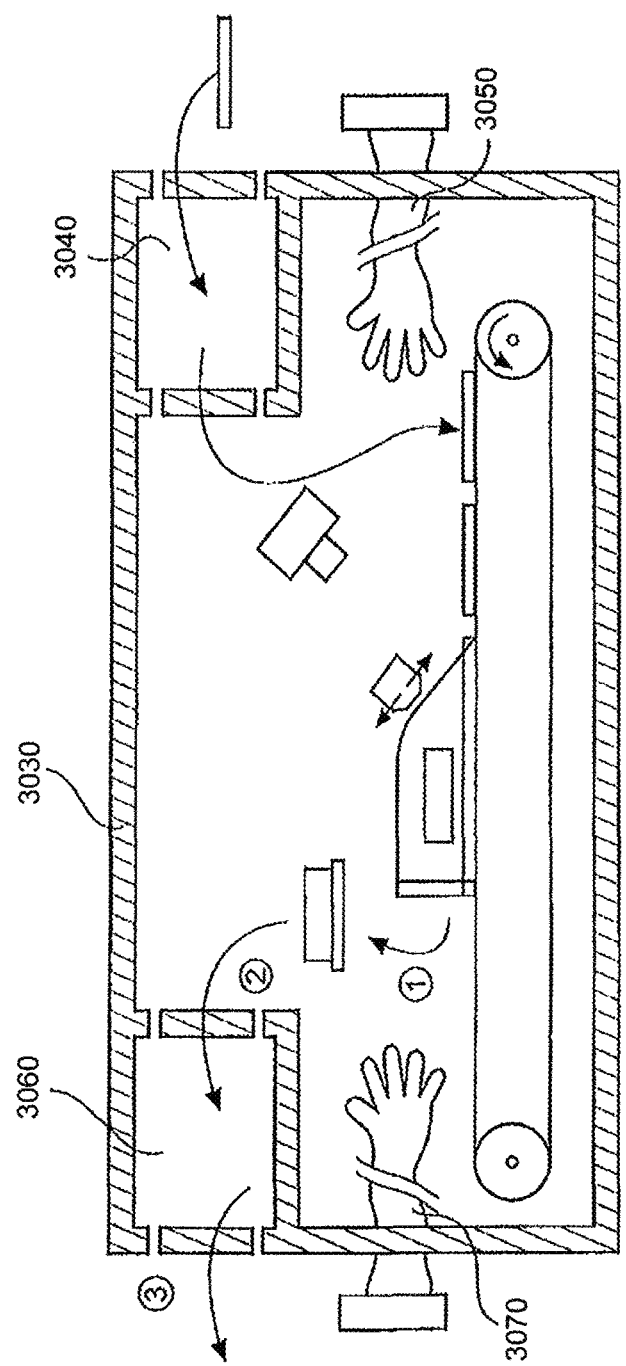
Figure 14:
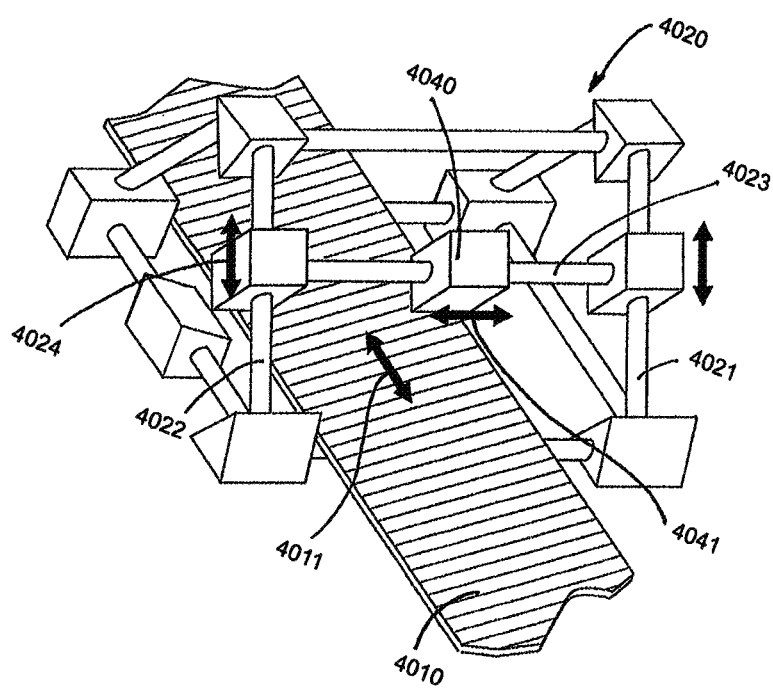
Figure 15:
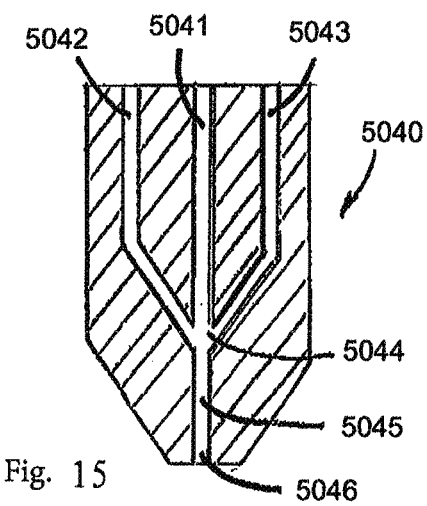
Figure 16:
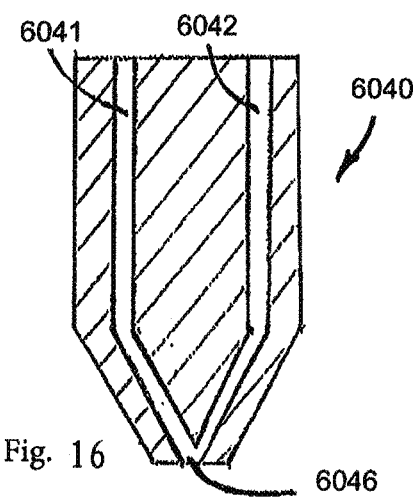
Figure 17:
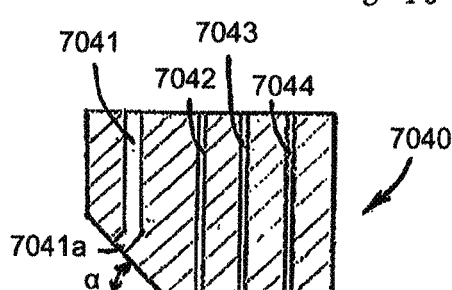
Figure 18:
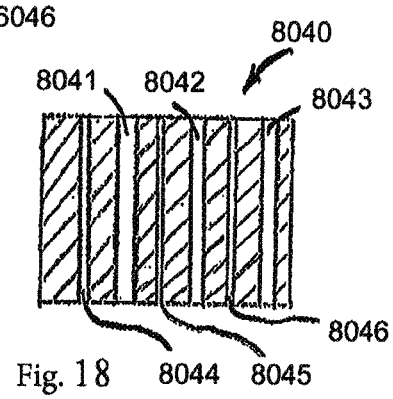

FIG. 6 a diagrammatic view of a production layout in accordance with a sixth embodiment of the invention, FIG. 7 a diagrammatic view of a production layout in accordance with a seventh embodiment of the invention, FIG. 8 an eighth embodiment o the invention, FIG. 9 a diagrammatic, lengthwise side view of a production section of a generative productive line in accordance with a ninth embodiment of the invention, FIG. 10 a schematic diagram of a production layout in accordance with a tenth embodiment of the invention, FIG. 11 a diagrammatic, lengthwise side view of a production section with endless conveyor belt, FIG. 12 a diagrammatic, lengthwise side view of a production section in accordance with an eleventh embodiment of the invention, FIG. 13 a diagrammatic display of a production layout in accordance with a twelfth embodiment of the invention, FIG. 14 a diagrammatic display of a production layout in accordance with a thirteenth embodiment of the invention, FIG. 15 a diagrammatic cut view of a first embodiment of a push button in accordance with the invention, FIG. 16 a diagrammatic cut view of a second embodiment of a push button in accordance with the invention, FIG. 17 a diagrammatic cut view of a third embodiment of a push button in accordance with the invention, FIG. 18 a diagrammatic cut view of a fourth embodiment of a push button in accordance with the invention.

V. DETAILED DESCRIPTION OF THE PREFERRED EMBODIMENTS

FIG. 1A shows a supporting device 20 for a total of eight inserts 10$a$-$h$, organized in two rows and four columns, as can be seen in FIG. 1B. Each insert 10$a$-$h$ has an individual height-adjustable substrate plate stack 12$a$-$f$. Each substrate plate stack 12$a$-$f$ is individually adjustable in height in a vertical direction 11 within its insert 10$a$-$f$. The vertical direction 11 is parallel to each other for each of the substrate plate stacks 12$a$-$f$, and vertical to the surface 13$a$-$f$ of the substrate plate stacks 12$a$-$f$, which are aligned horizontally, i.e. vertically to the direction of gravitational force.

Evaluations within the supporting device 20 are designed to accept one insert 10$a$-$f$ respectively in which a substrate plate stack 12$a$-$f$ is arranged. This, however, means that substrate plate stacks can also be used in the supporting device 20, which have a larger surface area of substrate plate 12$a$, for example a surface area which is twice as large or four times as large as the substrate plate stacks displayed in FIG. 1$a$, $b$ and which accordingly require two or four insertion places.

A filling block 12$g$, 12$h$ is included in the inserts 10$g$ and 10$h$ which does not display a substrate plate stack and is not used for the production of products.

Each substrate plate stack 12$a$-$f$ is height-adjustable via one actuator respectively 14$a$-$f$, which can for example be an electromotive driven linear actuator. The actuator 14$a$-$f$ is part of the insert 10$a$-$f$.

Each insert 10$a$-$f$ is encased in a housing, open to the top, rectangular in cross-section, and especially quadratic, which comprises four walls as illustrated for example by insert 10 $a$ through walls 15$a$-18$a$. Within these walls the substrate plate stack 12 $a$ moves and seals to the walls at its lateral edges in such a way that coating material applied to the substrate plate stack cannot penetrate between the substrate plate stack and the walls.

The upper edges of the walls close flush with a surface 21 of the supporting device 20 when the inserts 10$a$-$e$ are placed into the supporting device. Similarly, an upper surface of the insert 10$g$ is also flush to the surface 21 of the supporting device 20.

A powder coating device 30 is provided which comprises a powder conveyor 32 from which powder can be admitted to the surface 21 of the supporting device, and which also comprises a slider 33, which can move along a direction of motion reciprocally 31, across surface 21 and the substrate plate stack 12$a$-$f$ or inserts 10$a$-$h$. The slider 33 distributes the powder discharged by the powder conveyor 32 and applies a powder layer above the substrate plate stacks 12$a$-$f$.

The powder coating device 30 also comprises a collection device 34 for excess powder. The slider 33 pushes the powder into the collection device 34 which could not be applied as a powder coating above the substrate plate stacks.

As can be seen in FIG. 1A, the substrate plate stacks 12$a$-$f$ are set at different heights via their actuators 14$a$-$f$, i.e. the distance of the upper surface 13$a$-$f$ of each substrate plate stack to the level of the surface 21, along which the slider 33 moves and applies the powder as a coater, is different.

After each powder coating process, completed by the movement of the slider 33 from the right position shown in FIG. 1A to a, from this viewpoint, left position in the area of the collection tray 34, the layer coated in this powder-coating process above each substrate stack plate 12$a$-$f$ is cured in predefined areas via a radiation source, in this case a high-power laser 40. This selective curing is executed based on control data which corresponds to the cross-section of a product in the respective layer coated. In this selective curing process, the cured areas are connected to respective sections of the product underneath, which have been cured previously. The curing process can be made in particular as selective laser sintering or selective laser melting. However, other curing principles, such as for example photo-polymerization, can also be applied on the principle of the invention. The beam of the high-power laser 40 is controlled using beam-control means to ensure it hits the predefined sections of the respective layer previously coated, and selectively cures these sections above all previously coated substrate plate stacks.

The beam control means are coupled with a signal-related control device. Production data is stored in the control device for at least the products to be produced simultaneously. Production data especially comprises position data which characterize the position of the respective product on the substrate plate and geometric data which characterize the geometry of the respective product. Geometric data is prepared in such a way to ensure that geometric data of individual cross-sections of the product are included. The respective position of such a cross-section and the geometrical data stored for this cross-section corresponds to the position of the respective material layer coated from which this product is produced, and the geometry of the product in this material layer. In the embodiment shown with products standing vertically on the plate, the geometrical data therefore corresponds to the horizontal running cross-section planes through this product.

After curing of the selected sections, the slider 33 returns from the left position to the right position shown in FIG. 1A. The surface of the selectively cured sections are ground with a grinding unit fixed to the slider in order to achieve a defined surface for the subsequent coating and curing process and greater geometrical precision of the generatively produced component.

After this process, the substrate plate stacks 12a-f are lowered by a predefined distance which corresponds to the layer depth of the subsequently coated layer. As a result of this lowering process, the surface of the previously coated layer and the selectively cured sections in the layer are no longer flush with surface 21, along which the slider 33 moves with a lower coating edge, but by the distance at which the substrate plate stack was lowered, below the plane of this surface 21. A metered amount of powder is then discharged from the powder conveyor 32 to the surface 21 and, via movement of the slider 33 to the left of this powder, coated as a layer above the lowered substrate plate stack.

This process is repeated until a product is completed within the powder bed coated by layer in this way above a substrate plate stack. As can be seen in FIG. 1A, the time of completion of one or several products above the substrate plate stack is different in the different inserts 10a-f, in the example shown, the product or products on the substrate plate stack 12e in insert 10e are typically completed before the product or the products on the substrate plate stack 12c in insert 10c, in so far as the products completed in these have approximately the same height. The insert 10a is shown in the maximum raised position of the substrate plate stack 12a, which corresponds to production start.

After completion of the products on one individual insert 10a-f, this respective insert can be removed from the supporting device 20 and replaced with a new insert, whose substrate plate is in the top position. The products in the removed insert can be separated from the substrate plate after non-cured powder material has been removed. New products can be simultaneously produced on the new stack applied. As a result of such potential of delayed and simultaneous curing of products in the device, high productivity is achieved in the generative production of products.

FIG. 2 shows a second embodiment of the invention in which several substrate plate stacks 112a-c can be coupled to an endless conveyor belt 120 as modules 110a-c. Several coupling points 122a, b, c, d . . . are provided on the conveyor belt 120 which also serve as an fixing device for a module 110a-c and provide power supply for an actuator 114a-c included in the module.

The actuator within each module is designed so that each substrate plate stack 112a-c can be adjusted in height individually.

As can be seen in FIG. 2, the substrate plate stacks 112a and 112 b are designed as individual stacks, while the substrate plate stack 112c is designed as a twin-stack and covers twice the length along the conveyor belt 120.

Each module 110a-c is fitted with side walls, like the inserts in accordance with FIG. 1A, B, within which the substrate plate stacks 112a-c can move vertically with edges sealed. The upper edge of the edge walls close flush with a surface 121 from which a powder conveyer 132 can discharge powder. The surface 121 is horizontal, i.e. vertical to the direction of gravitational force and via movement of a slider 133 with a bottom coater edge which rests on the surface 121, the coated powder is distributed in one direction 131 across the substrate plate stack 112a-c and finally, after the slider has moved from the right position shown in FIG. 2 to a horizontally left position, excess powder is pushed into a collection tray 134.

Again, also in the embodiment displayed in FIG. 2 a different height of powder bed is set in each individual module 110a-c by way of gradation lowering of the substrate plate stacks 112a-c in a respective individual way, and as a result a different level of production progress is achieved, i.e. the layer coated in a working work cycle of the slider 133 shows a distance to the upper surface of the substrate plate stack 112c which is different to the distance to the surface of the substrate plate stack 112b, which in turn is different o the surface of the substrate plate stack 112a. In this way products can be generatively created with different levels of production progress or in different production stages in the individual modules, as can be seen in module 110a shortly before completion of the product 160, 161a and the product 160 b almost half completed in module 110 b.

For the functioning of the production layout in accordance with FIG. 2 it is planned that production progress in modules 110a-c starting from the right in the direction of conveyance of the conveyor belt 120 increases to the left, as shown by arrow 123. As soon as completion of products has been achieved in a production module, the conveyor belt continues to move until this module can be removed, or the module is removed and the conveyor belt moved on by the respective length of the module. In such a case, a new module can be inserted on the right side adjacent to the position displayed of the slider 133, and generative production can be started in this module. The removed module can be processed in a further production section, in particular the non-cured powder material can be removed and the products completed in this can be removed from the substrate plate stack. The special advantage of this is that in the completed substrate plate stack, which was previously subjected to simultaneous production with the other substrate plate stacks, the non-cured powder and the completed products can be removed, without the powder from other substrate plate stacks having to be removed and without the need to stop the manufacturing process in the other substrate plate stacks.

FIG. 3 shows another embodiment of the invention. In a manner compliant with the embodiments of FIGS. 1A, B and 2, several substrate plate stacks 212a-c are arranged next to each other and encased respectively by side walls in a sealed manner to the edges of each substrate plate stack. The upper edges of the side walls close flush to a surface 221, along which a slider 233 of a powder coating device moves along one direction 231, and in which its lower edge serves as a coater. The slider 233 coats the powder layer above the substrate plate stack 212a-c in one working stroke, and pushes excess powder into a collection tray 234.

A laser beam source 240 is also provided which serves to selectively cure predefined areas of the coated powder layer above the substrate plate stack. Control of the production device is provided which is designed so that, after each coating layer process, predefined areas above the substrate plate stack are cured by means of a laser beam source 240, as described above.

In contrast to the embodiments shown in FIGS. 1A, B and 2, for the embodiment in accordance with FIG. 3 there is an actuator 214 a-c which serves to provide individual height adjustment for the substrate plate stacks 212a-c and thus to individually change the distance of the upper surface of the respective substrate plate stack from the plane at which the coater edge of slider 133 is moving, and is not a component of a module inserted in a supporting device. Instead, these actuators 214a-c are integrated in the supporting device 220 and the substrate plate stacks 212a-c are detachable and can be coupled to the actuators 214a-c.

With the embodiment shown in FIG. 3, in the same way a quasi continuous production of products can take place via a generative production process such as SLS (Selective Laser Sintering) or SLM (Selective Laser Melting), whereby products are made simultaneously in several substrate plate stacks which are at a different stage of production for each substrate plate stack. This is achieved by way of the substrate plates stacks being able to be adjusted individually in height, which in turn means that a powder bed is coated above each substrate plate stack whose height is different between adjacent substrate plate stacks, even though the respective new layers of curable material are coated by just one slider 133 in just one working cycle onto several substrate plate stacks 212a-c.

FIG. 4 shows a forth embodiment of the invention which has certain specific individual characteristics. The embodiment shown in FIG. 4 is based on the same principle as that used in the embodiments shown in FIGS. 1A-3 and has a substrate plate stack 312a, which can be positioned adjacent to other substrate plate stacks (not shown) and can be individually adjusted in terms of height. This means that the following principle explained concerning FIG. 4 can be applied to the embodiments explained in the FIGS. 1A-3

FIG. 4 shows a first metering module 310a which serves as a metering platform and which is filled with powder before the start of a production process. For this purpose, a height-adjustable base plate 312a is inserted within the metering module at the lowest position. Above the metering module 310a there is a radiation field 380 which pre-heats the powder filled into the metering module 310a.

A coater 333 can be slid horizontally along one direction 331. A heating band 335 is located in the direction of movement in front of the coater 333 which continuously heats the powder moved by the coater or maintains the powder at the pre-heated temperature.

Adjacent to the metering module 310a, the substrate plate stack 312b is located in a component module 310b. The substrate plate stack 312b can be shifted vertically in the component module 310a individually and independent of the base plate 312a.

The component module 310b, in relation to the direction of movement 331 of the coater 333, is between the metering module 310a and a collection module 310c, which serves to collect excess powder pushed beyond the component module 310b by the coater 333. A base plate 312c is also located in the collection module 310c, which can be shifted vertically individually and independent of the base plate 312a and the substrate plate stack 312b.

In principle this means that the embodiment shown in FIG. 4 can have several such component modules of substrate plate stacks instead of the individual component module 310b displayed with substrate plate stack 312b. These several component modules would be located next to each other in the direction of coating 313 and the majority of substrate plate stacks would in total be placed between a metering module 310a located at one end in relation to the path of shifting 331 of the coater 333 and a collection module 310c located at the other end.

A radiation field 380c is also located outside the collection module 310c, which serves to keep the excess material collected in the collection module at a defined temperature.

A heating unit 315b is integrated in the substrate plate stack 312b which keeps the substrate plate stack and the respective powder bed on it at a defined temperature.

The embodiment shown in FIG. 4 is optimized in that a defined, pre-heated powder status of the powder is achieved before the selective curing process, by means of provision of the radiation fields 380a, b the heating band 335 and the heating unit 315b.

The manufacturing process possible with the embodiment shown in FIG. 4 consists of a sequence in which initially the substrate plate stack 312b is lowered by an amount which corresponds to the coating layer to be applied, and the platform 312a of the metering module 315a is raised by a specific amount which is calculated from the cross-section of the platform and the powder volume required for the subsequent coating process.

Following this, the pre-heated powder volume from the area of the metering module is pushed via horizontal movement of the coater 333 across the substrate plate stack 312b and a layer is coated on the substrate plate stack 312b or, where appropriate, other substrate plate stacks. Excess powder is moved into the collection module.

After this powder layer has been applied, the powder layer is selectively cured in predefined areas by a laser 340 and the cured areas are connected to previously cured areas in the layer located underneath.

The coater 333 then moves back, whereby the surface of the previously cured areas are ground by means of a grinding unit located in front of the coater in the subsequent movement of direction from left to right, in order to improve geometric precision of the generatively produced product and to increase the connection of the areas to be subsequently cured on it. Alternatively to this form in which the grinding process is executed in a reverse cycle of the coating device, it is possible to execute the grinding process together with the production stage of the fresh powder coating. In such a case the location of the grinding unit to the coating device is to be designed so that the grinding unit is in front of the position on which the powder is coated in the direction of movement of powder coating.

After the coater 333 has returned to its right position shown in FIG. 4, the process starts again and is repeated until the product to be made above the substrate plate stack 312b or, if appropriate, another substrate plate stack located in a row of substrate plate stacks has been completed. The laser beam of the laser beam source 340 is selectively applied across every layer so that pre-defined areas of this layer, which correspond to the cross-section of the product to be made in the respective layer on all substrate plate stacks, are selectively cured.

On completion of the manufacturing process, the product can be separated from the substrate plate stack. This means that several products can also be produced above one substrate plate stack, and that several substrate plate stacks next to each other can be coated with just one coater 333 in different production stages and can be selectively cured with one laser 340.

The powder collected in the collection module 310c can be raised by lifting the platform 312c and, by means of appropriate process of the coater 333 from left to right, can be returned to the metering insert, to start a new production process and to re-use the powder. Alternatively, in the subsequent manufacturing process the functions of metering module and collection module can be exchanged so that the coating application process is now executed by movement of the coater from left to right, and the grinding process by the opposite direction, i.e. from right to left. In such a case the mobile unit consisting of heating band, coater and grinding unit is to be designed so as to be adjustable, preferably by 180° around a vertical axis.

FIG. 5 shows another embodiment of the invention. The production layout shown in FIG. 5 comprises a process chamber 1000 which has a first lock 1010 and a second lock 1020.

Substrate plate stacks are fed through the first lock 1010 and placed on a conveyor belt 1030. The substrate plate stacks are stored intermediately on this conveyor belt and can, if necessary, be pre-heated.

By means of a robot arm 1040, the substrate plate stacks can be placed on a construction platform 420b of a construction insert 410b, in order to produce generative products on this. The construction insert 410b, as described above with regard to the embodiment pursuant to FIG. 4 relating to the three modules 312a-c shown there, is flanked by a metering insert 410a and a collection insert 410c, which means that also several substrate plate stacks can be placed next to each other between the metering insert and the collection insert in order to execute quasi continuous production in the method described above.

After completion of the generatively made products in the construction insert, the substrate plate stack 412b can be moved to a lower position in the embodiment shown in FIG. 5. In this lower position, the construction space above the substrate plate stack 412b is in connection with a powder suction channel 490 which is recessed in the wall thickness, and which limits the construction space as a side wall. Above this powder suction channel 490, the powder not cured can be sucked from the area above the substrate plate stack 412b.

The powder suction channel 490 is also designed so that the powder pushed into the collection insert can be sucked by the suction channel 490, whereby this may or may not be provided as an additional optional function. In this context, reference is especially made to the different operating modes of the embodiment with metering module and collection module, which were explained for the embodiment pursuant to FIG. 4.

After the non-cured powder has been sucked from the area above the substrate plate stack 412b, the construction platform can be moved vertically into the upper position, and the substrate plate stack 412b can be grabbed by the robot arm 1040 and fed to a second conveyor belt 1050.

With the second conveyor belt 1050, the substrate plate stack 412b together with the products located on it is conveyed through an annealing furnace 1060 to subject the products on it to post-curing and thus to produce the defined component characteristics. After post-curing has been completed, the substrate plate stack 412b can be discharged out of the process chamber 1000 through the lock 1020.

By means of the structure in accordance with FIG. 5 it is possible to execute pre-heating and provision of the plates as well as the entire generative manufacturing and powder handling and subsequent annealing in a controlled atmosphere, especially in an inert gas or active gas atmosphere, within a process chamber 1000.

FIG. 6 shows a further aspect of the device or process in accordance with the invention. FIG. 6 shows four substrate plate stacks 512a-d positioned in two rows and two columns. As can be seen, each of the substrate plate stacks can be adjusted individually in height by means of a respective lifting/lowering device 514a-d for each plate. Both the substrate plate stacks of a row and the substrate plate stacks of a column can be moved vertically independently of each other, so that products can be made generatively in different production stages on each of the substrate plate stacks.

Dividing walls are to be provided between the respective substrate plate stacks for individual structure of a powder bed above the respective substrate plate stack. In the embodiment shown, the dividing walls are not part of the device, but the dividing walls are continuously developed by selective curing of the powder material at the edge area of the respective substrate plate stack, and consequently increase vertically in the middle area of the substrate plate stack with the generatively manufactured product. Alternatively, it can be planned that dividing walls are provided as part of the production device and are positioned so that their top edge closes flush with a plane on which a powder coater moves.

FIG. 7 shows a seventh embodiment of the invention. The embodiment has an endless conveyor belt 620 along which several substrate plate stacks 612a-e are located in the direction of conveyance 621.

The substrate plate stacks 612a-e are positioned so that their top surface is on one plane.

Above the substrate plate stacks 612a-e, several coating devices 630a-d are positioned. The individual coating devices 630a-d each comprises a coater 633a-d. The bottom edge of the coater 633a is positioned at the distance of a layer from the surface of the substrate plate stacks 612a-e. The bottom edge of the coater 633b is distanced one shift distance more from the surface of the substrate plate stack 612a-e compared to the pervious coater 633a, and in the same way the bottom edges of coater 633c, d are raised appropriately one layer depth more from the surface of the substrate plate stack compared to the previous, adjacent coater.

The embodiment shown in FIG. 7 displays a range of adjacently positioned individual coating devices a, b, c, d . . . provided in such a vertically staggered height arrangement.

There is an area between two respective coating layer devices 633a, b, c . . . , in which the coated layer can be selectively cured using a laser 640a, b, c, d. One respective laser is to be allocated to each individual coating device.

The conveyor belt 620 is moved continuously or discontinuously during manufacture in such a way that the carrying run in the constellation shown in FIG. 7 moves from right to left.

This means that above the substrate plate stacks 612a, b, c . . . a material bed is coated via layers applied on top of each other, which becomes higher the further a substrate plate stack is conveyed by the conveyor belt from right to left. Accordingly, the construction height of the generatively manufactured product on the respective substrate plate stack increases.

The principle of the embodiment shown in FIG. 7 shows that, by means of the multitude of powder coating devices and the total of layers coated with these powder coating devices in one movement cycle of the conveyor belt, the defined height of the powder bed and thus the manufactured products can be achieved. Alternatively, the conveyor belt 620 can also be moved several times back and forth reciprocally during the manufacturing process, whereby the several powder coating devices or the conveyor belt are shifted vertically in order to apply a number of M×N powder layers by means of a number of N powder coating devices during the manufacturing process, where M corresponds to the number of reciprocal movements of the conveyor belt. This means that the N powder coating devices are raised by one amount after each reciprocal movement of the conveyor belt or the conveyor belt is lowered by such an amount, which corresponds to N-times of layer thickness, in order to ensure that the powder coating device furthest right and thus at the lowest position, applies its layer in the subsequent coating process onto the layer coated by the powder coating devices positioned previously furthest left, and thus highest.

After respective completion of the product, in the direction of conveyance to the left of the conveyor belt 520 there follows a suction of non-cured powder material 590 from the area above the substrate plate stack, on which finished products are positioned. This means that powder suction only takes place above the substrate plates stack positioned furthest left, while the substrate plate stack to the right is not yet sucked on account of the products which are normally not yet completed. This can be achieved via respective parallel positioned dividing walls between the substrate plate stacks.

After sucking off the non-cured powder, the products made on the substrate plate stack can be separated from the plate. If required, after this separation process, the surfaces of the substrate plate stack can be again prepared plane via a device for surface smoothing positioned to the left of the suction, especially a milling or grinding station or a device for laser smoothing, so as to feed the substrate plate stack a new generative manufacturing process.

This means that the several radiation sources can be provided respectively via individual laser sources or via one or several laser sources whose beam can be split and therefore aimed at several positions. This means that the divided beam and the resultant multiple courses of beam generated can also be guided individually across the respective layers via appropriate beam guiding means in order to selectively cure each layer individually. In accordance with the invention, the layer coating process for all substrate plate stacks takes place in a common first working cycle, followed by a selective curing process in a second working cycle. This can be executed with an appropriate number of individual coating devices via continuous movement of the conveyor belt or—in the case of reciprocal movement of the conveyor belt—in a quasi continuous process.

FIG. 8 shows a further embodiment of the invention. In this embodiment several substrate plate stacks 712a, b are positioned on top of each other and the construction space above the respective substrate plate stacks is limited by common side walls 715-718. The substrate plate stacks 712a, b . . . move in a vertical direction from top to bottom through construction space limited by the side walls. By means of a layer coating device, layers are repeatedly coated in the construction space created respectively above the upper substrate plate stack 712b and selectively cured via a laser beam source. The layer coating process can be carried out in the same way as described above by means of a coater. This coater moves along a horizontal plane in the embodiment shown in FIG. 8, i.e. vertical to the direction of conveyance of the substrate plate stacks 712a, b.

As soon as a sufficiently high powder bed has been applied above the substrate plate stack and the product generatively manufactured and embedded therein has been completed, a new substrate plate stack can be placed on it, whereby it is respectively coupled for vertical movement to a conveyance device.

The substrate plate stacks with the completed products on top can be removed in a production stage below the layer coating device and the construction space in which generative manufacturing takes place, by means of the powder being sucked off and the products separated from the substrate plate stack. Channel suction in particular can be applied, as explained in relation to FIG. 5, in order to then convey the products to an area which is not limited by side walls, which means it is possible to remove the products or the entire substrate plate stack from the vertical conveyance device.

FIG. 9 shows a substrate plate stack 2010 consisting of several substrate plate stacks 10a-c. The substrate plate stacks 2010a-c can be detached and are connected to a substrate plate carrier 2020 positioned beneath. The substrate plate carrier 2020 and the substrate plate stacks 2010a-c are arranged so that the surface of the substrate plate stacks 2010a-c are designed horizontally when the device is operating, i.e. vertical to the direction of gravitational force.

A coating device 2030 is positioned in the direction of gravitational force above the top layer surface of the substrate plate stacks 2010a-c. The coating device 2030 is can be shifted along a direction of movement 2031. The direction of movement 2031 is linear and compasses an angle $\alpha$ with the plane defined by the upper layer of the substrate plate stacks 2010a-c. By means of cyclical back and forth movement of the coating device 2030 along the direction of movement 2031 a powder coating can be applied above the substrate plate stack s 2010a-c at an angle inclined $\alpha$ to the horizontal.

A heating unit can be installed in each substrate plate stack 2010a-c, which keeps the substrate plate stack and the powder bed on top at a defined temperature. By means of this and by one or several additional radiation fields and/or heating bands provided in the section of the coating device, which heat the powder coating applied or keep it at a specific temperature, the device can be optimized to ensure that a defined, pre-heated powder status of the powder is achieved before the selective curing process.

The substrate plate stacks 2010a-c can be moved continuously or in a cyclical, quasi continuous manner in one direction of movement 2011 which is parallel to the horizontal. By means of the direction of movement 2011, after the coating of a layer, the coating device 2030 ensures a distance between the level in which the coating device 2030 moves and generates the layer coated which corresponds to the layer height of the next layer to be applied.

A radiation source 2040, which is a high-power laser, is positioned so that its beam hits the surface of a coated layer approximately vertically, or preferably exactly vertically. The beam of the radiation source 2040 can be controlled using beam guiding means so that it hits predefined areas of a coated layer and selectively cures these areas.

The beam guiding means are coupled in signal terms with a control device. Manufacturing data are stored in the control device for at least the products to be manufactured simultaneously. Manufacturing data in particular comprise position data which characterize the position of the respective product on the substrate plate, and geometrical data which characterize the geometry of the respective product. The geometric data is prepared so that these include geometric data of individual cross-sections of the product. The respective position of such a cross-section and the geometric data stored for this cross-section corresponds to the position of the respective material layer applied from which this product cross-section is manufactured, and the geometry of the product in this material layer. In the embodiment shown with products positioned vertically on the plate, the geometrical data therefore corresponds to oblique running cross-section planes through this product.

As can be seen, as powder bed is applied above the substrate plate stack 2010c, composed of several powder coating layers and which has the maximum height h above the substrate plate stacks. Above the substrate plate stack 2010b this maximum height is already reached in an area to the left, but is not completely reached in a section to the right of this, positioned against the direction of conveyance 2011. Instead, the surface of the powder bed in this right section of the substrate plate stack 2010b runs inclined at an angle α1, in the same way as in a left section of the substrate plate stack 2010c.

Above the substrate plate segment 2010b there is an additively manufactured product 2060b aligned in a powder bed in cured form. A product 2060c is additively manufactured in the same manner above the 2010a. This manufacturing process is realized in that after application of each powder layer 1051 predefined areas of this powder layer will be cured selectively by the radiation source 2040. Following thereupon, by feed of the substrate plate segments in the conveying direction 2011, a distance is spaced corresponding to the height of the layer between the level of the coating device 2030 and the previously applied layer. Then follows another coating process realized by moving the coating device 2030 along the direction of movement 2031. On the coating device, a grinding instrument can be assembled with preference, aligned either in the direction of movement of powder coating ahead of the position where the powder is applied, and which serves and is designed to superficially grind the previously cured areas. Thereby, the additively manufactured product will be true to geometry, and the connection of the areas to be cured after that it will be improved. Alternatively, it is possible to make the grinding process in a return feed process of the coating device. This means between the production step of the selective curing and the production step of the repeated powder coating. In which case the alignment of the grinding instrument at the coating device can be chosen freely for construction with reference to the position where the powder is applied, as the grinding process and the powder application process do not take place during the same movement of the coating device.

This process is repeated until the entire product 60c is manufactured. The conveying movement 2011 moves the products 2060b, c thus additively manufactured and finished to the left, where after removal of the non-cured powder they can be removed from the substrate plate.

FIG. 10 in this regard shows one potential structure of a production line and related process flow. As can be seen, the substrate plate segments 2010a, b, c . . . are sluiced in from the right side in a horizontal direction of movement 2011 to an entry sluice 3000. In the same direction of movement 2011 they come from the entry sluice 3000 into a process chamber 3010. The process chamber 3010 accommodates the production segment represented in FIG. 9. The manufacturing process explained for FIG. 1 also takes place there. After the corresponding additive manufacturing of the products in the process chamber 3010 they are conveyed with another movement along the direction of movement 2011 to an outlet sluice 3020 from where they will be sluiced out of the process chamber.

By sluicing in the uncoated substrate plate segments through the entry sluice 3000 and by sluicing out the coated the substrate plate segments furnished with additively manufactured products through the outlet sluice 3020 it is possible to maintain an atmosphere in the process chamber 3010 which is beneficial for additive manufacturing, in particular an inert gas atmosphere or an active gas atmosphere in order to secure the product quality.

FIG. 11 shows a second design form of a production section for additive manufacturing and a production section for separating and removing additively manufactured products. A majority of the substrate plate segments 2010a, b, c . . . is aligned one next to the other thus providing a continuous the substrate plate. The top surface of this substrate plate furnished by the substrate plate segment segments 2010a, b, c . . . is oblique in an angle α to the horizontal axis, which means this surface is in an angle 90°-α to the direction of gravity.

Above the substrate plate segments 2010a, b, c . . . there is a coating device 2130 which can move cyclically along a horizontal direction of movement 2131. With the coating device 2130 a powder layer is applied from a powder reservoir which can be positioned either on the coating device 2130 or along the path of movement 2131 of the coating device 2130.

With the coating device 2130 a powder layer can be applied above the substrate plate segments 2010a, b, c . . . by moving it along the coating device 2131, which powder layer then lies in an angle α to the top surface of the substrate plate segments.

On the substrate plate segments 2010a, b, c . . . by selective curing of each applied layer with two radiation sources 2140a, b designed as high-performance lasers, predefined areas of each powder layer are cured selectively, and thereby the products 2060a, b are built additively and layer wise on the substrate plate segments. Furthermore, between every product, or between a group of products, dividing walls 2061a, b are built above the substrate plate segment s by corresponding selective curing of the layers. These dividing walls divide the powder bed above the substrate plate segments into several powder bed areas. One or several products are positioned in each powder bed area and can be removed simultaneously.

The substrate plate segments 2010a, b, c . . . are fastened on an endless conveyor device 2120 and this endless conveyor device 2120 continuously or discontinuously moves them in the conveying direction 2111. A production segment A, through this conveying movement 2121 and repeated application of powder layers by the coating device 2130, followed by selective curing of each applied layer, realizes the additive manufacturing of the products. The powder coating device 2130 therefore moves along a direction of movement 2131 positioned in an angle α2 to the direction of movement 2121 of the substrate plate segments.

In a production segment B non-cured powder material is removed by a suction device from this segment between two additively manufactured dividing walls 2061a-d and following that, the dividing walls as well as the products additively manufactured and finished in this segment between the two dividing walls are removed. In the conveying direction 2121 behind the production segment B the substrate plate segments are steered along a guide pulley into the lower run of the conveyor device 2120 and they glide along this lower run to a second guide pulley to be steered into the upper run from where they are steered to another coating process with powder coatings and additive manufacturing of products.

A collector basin 2170 is provided to collect excess powder which gathers during the movement of the substrate plate segments.

As can be seen in FIG. 11 individual products can be built additively on one single substrate plate segment, or a single product can be built on several substrate plate segments. It only depends on the size of the substrate plate segments and the products additively manufactured thereon whether several products are built on one substrate plate segment or one product is manufactured on several substrate plate segments, or one product per substrate plate segment. By use of supports, it is also particularly possible to manufacture one product on one single substrate plate segment with dimensions bigger than the dimensions of the substrate plate segment.

The embodiment shown in FIG. 11 is in particular well suited for use in stereolithography. In both design forms represented in FIG. 9 and in FIG. 11 the angle α1 respectively α2 between the direction of coating application and surface of the substrate plate segments is smaller than the dumping angle of the applied powder to provide stability of the applied powder bed against the effects of gravity. In general, in the design form represented in FIG. 11 the angle α2 might also be selected bigger than this dumping angle of the powder, as the powder bed is stabilized by the dividing walls 2061a-d and the powder layers are applied and lay horizontally.

FIG. 12 shows a schematic representation of an alternative design form in which the angle α3 between the level of powder layer application and the surface of the substrate plate segments might be bigger than the dumping angle of the powder. In this design form, the products 2260a-c are also additively manufactured on the substrate plate segments 2210a-c and thereby a powder bed 2250 is manufactured above these the substrate plate segments. The powder bed 2250 is stabilized by a cover plate 2280 which runs in parallel to the substrate plate segments in the production section. Wherein the cover plate 2280 in particular can move forward continuously with the substrate plate segments in order to prevent a relative movement between the powder bed and the cover plate 2280.

FIG. 13 shows a schematic representation of a production alignment for continuous production of additively manufactured products. The design form according to FIG. 13 represents an alternative to the design form represented in FIG. 10. In contrast to the design form represented in FIG. 10 the design form represented in FIG. 13 all production sections required for additive manufacturing and removal of the products from the additive manufacturing process are aligned within a process chamber 3030 which can be kept under a controlled atmosphere, in particular under an inert gas or active gas atmosphere.

As can be seen a manufacturing process is aligned within the process chamber 3030 and its underlying principle corresponds to the manufacturing process according to FIG. 9. However it is to be understood that the production alignment represented in FIG. 13 can be designed in the same way so that a manufacturing process according to FIG. 11 or FIG. 12 takes place in the process chamber. The process chamber 3030 accommodates the first sluice 3040 through which new, uncoated substrate plates not yet furnished with products can be sluiced in and can be fastened on an endless conveyor device. In order to be able to make this process manually, a working glove 3050 is positioned gas-tight in such a section and it allows to take up the substrate plates from sluice 3040 and to fasten them on the endless conveyor device.

A second sluice 3060 is further positioned in the process chamber 3030. The substrate plates with finished products positioned on them can be sluiced out through sluice 3060 out of the process chamber 3030. In order to be able to make this process manually, again a glove is positioned in the area of sluice 3060, where an operator can intervene in the process chamber 3030, loosen the substrate plate segments together with the products on them from the endless conveyor device, and sluice them through sluice 3060 out of process chamber 3030.

In the other design form represented in FIG. 14 the substrate plate 4010 is designed as an endless conveyor device and it runs in direction 4011 through a frame rack 4020. The frame rack 4020 is designed as a profile structure with triangular cross section, with a base in parallel to the surface of the endless conveyor device.

On two frame supports 4021, 4022 oblique to the base plate a guide rod 4023 is positioned with bearing and can be moved along direction 4024. The guide rod when moved along the supports 4021, 4022 passes over a surface oblique to the surface of the endless conveyor device 4010, on which the products are build additively. With preference, the declination of this surface can be regulated in order to adjust it to different materials and product forms. For time-efficient production of long components it is better to align them lengthways in parallel to the substrate plate, and to set a small declination angle. For faster production of several smaller products it would be better to set a bigger angle in order to allow one product is finished and removed while the next product is still in production.

A printing head 4040 is fastened on the guide rod 4023 and with bearing so that it can be moved along the guide rod 4023 in direction 4041. The printing head 4040 is designed for selectively applying material. Thereby a material is applied to certain areas of a layer on which it cures. This curing—depending on type and quality of the applied material—can be realized by drying or chemical curing in air, by cooling from melting liquid condition, by reaction between two reagents contained in the material, or by other chemical or physical processes.

The device according to FIG. 14 provides an alignment for additive manufacturing in which a printing head can be moved freely in one level which is oblique to a the substrate plate surface, and is stretched out by the directions 4024 and 4041. The printing head by applying material on the substrate plate surface or on layers built obliquely on it, manufactures a product layer-wise. The printing head therefore is positioned on a frame rack the dimensions of which are chosen so that the substrate plate can be passed through this frame, and in particular it can be designed as an endless conveyor device passing through the frame.

In this way, this device makes it possible in a simple form to manufacture products of very long length additively by building these products under a horizontal feed direction of the substrate plate. The products can be built directly on the substrate plate surface, or optional above the substrate plate surface, and they can be manufactured next to each other, after each other, or off-set on top of each other. It might be desired to support the products mutually with auxiliary structures to secure their position and to increase the precision of production, and these auxiliary structures preferably should have a predetermined breaking point to make it easier to remove them later.

The device represented in FIG. 14 is also particularly suited for manufacturing three-dimensional products in a first application mode in the aforementioned manner also to realize the printing of printing carriers in a second application mode. Therefore the axis 4023 of the printing head 4040 is transported into a fixed position along the direction of movement in 4024 so that the axis 4023 stands fast during the printing. The conveyor device 4010 can convey a sheet of paper, or a slide or similar materials as printing carriers in the conveying direction 4011, and thereby the movement of the printing head 4040 along axis 4023 in combination with the movement along the conveying direction 4011 can make a two-dimensional print by dispersing one color or several colors to the paper/the slide.

In that it has to be understood that the oblique position of axis 4022 as represented in FIG. 14 and the related direction of movement 4024 are not necessarily required for designing the device for 3D-printing and 2D-printing in a first and second application mode. Instead, other geometries, in particular geometries in which axis 4022 is perpendicular to the conveyor device, are also feasible without causing a loss of the option to chose one or three-dimensional printing for production printed printing carriers or three-dimensional products.

The device according to FIG. 14 is also particularly suited for manufacturing in a third application mode selectively colored three-dimensional products with individual geometries. For this purpose, the printing head 4040 is provided with a color steering duct and a line duct for curable material. The color then can be added to the curable material either directly in the printing head 4040 to be dispersed together with it, or it can be dispersed separately from its own opening outlet from the printing head 4040 to a layer already applied.

FIGS. 15 to 18 show different variants of printing heads in cross sections, which are suited for the device/the process for an alternatively three-dimensional or two-dimensional print in two different application modes.

FIG. 15 shows a variant where a printing head 5040 has a central inlet duct 5041 for curable material. Aligned on the side or for instance on a circle track around the central duct 5041 there is one or there are several color inlet ducts 5042, 5043, into which a printing color can be fed in dosages. These printing colors preferably can be the standard color formulas for mixing all kinds of colors, for instance a color formula according to the RGB-color scheme or according to the CMYK-color scheme. For reasons of efficiency and costs, a color duct for black color can also be foreseen.

The color ducts 5042, 5043 at a mixing station 5044 flow into the central duct 5041. The material mixed at that station from there flows through a joint central outlet duct 5045 to an outlet nozzle 5046.

With a printing head of this design, by adding several colors in determined doses and one or several curable materials through corresponding dosing units from color containers or material containers in the printing head, a defined mix can be manufactured from the curable material and the colors, to provide selective coloring for individually manufactured three-dimensional products. Through corresponding controlling, optional uncolored, and in particular colorless three-dimensional products can be manufactured by feeding only curable material only, or a mere two-dimensional color print can be manufactured by feeding only color.

FIG. 16 shows another design form of a printing head 6040 according to invention. This printing head has tow or several feeding ducts 6041, 6042 which end in a joint nozzle 6046. Either only curable material, only color, or a mix of curable material and color is fed into the feeding ducts 6041, 6042 through a dosing and mixing station ahead of the printing head 6040, dispensed from nozzle 6046. The printing head, in the same way as the printing head 5040 described above, enables three application modes in the aforementioned manner, and it differs from the printing head 5040 in that the materials are added from a dosing and mixing unit away from the printing head, and this allows a more compact design of the printing head.

FIG. 17 shows a design form which provides in total 4 ducts 7041-7044 in a printing head 7040. The duct 7041 is designed for feeding and dispersing a curable material for three-dimensional printing, and it ends in nozzle 7041a. The ducts 7042-7044 are provided for feeding and dispersing color from the printing head 7040 and they end in the related color dispenser nozzles 7042a-7044a. It has to be understood that these color ducts 7042-7044 can be grouped together inside the printing head, to end in a joint dispenser nozzle.

The material supply duct 7041 ends in a nozzle 7041a, which is positioned on a surface 7047 of the printing head 7040. This surface 7047 is oblique in an angle α towards the surface 7048, where the color ducts 7042-7044 end. The design of the printing head 7040 by virtue of this form is particularly suited for producing three-dimensional products in a continuous manufacturing process, in which the application level is oblique to the feeding direction, which is realized between two layer applications, in particular where 7040 in the same way is suited for realizing three application modes as described above. Different to the realization with the printing heads 5040 and 6040 however, printing with printing head 7040 for production of selectively colored individual three-dimensional products, the color is applied separately on an already applied layer of the curable material, while optionally it is applied on a material layer previously applied through application nozzle 7041a but not yet fully cured, in order to realize penetration of the color into the curable material prior to curing, or by applying the color onto an already cured layer, to be sealed afterwards by coating it with a curable material.

FIG. 18 finally represents a fourth design form of a printing head 8040 in which a multiple number of line ducts 8041-8043 for curable material and a multiple number of line ducts 8044-8046 for color are provided in a parallel alignment next to each other. The ducts for material and color are positioned alternately one next to the other. With this printing head, an individual three-dimensional product or a two-dimensional print can be realized on a printing carrier in the fashion of matrix printing I, fast and efficiently. Thereby the first and second application mode and the third application mode can be realized and through suitably tight alignment of the nozzles to each other, a simultaneous application of color and curable material for production of selectively colored individual three-dimensional products is also possible. In the same way, the printing head 8040 is also suited for production with time-offset of such selective colorings on three-dimensional products as described above for the printing head 7040.

The printing heads described above are also suited for applying a multiple number of different curable materials, for instance materials with different mechanical, electrical, chemical characteristics, or materials with identical characteristics in different colors, to mix, for instance in a RGB-color scheme, a curable material of any desired color.

On principle, the printing heads 5040-8040 described above can also be used instead of the printing head 4040 in the device according to FIG. 14 and then they can be moved along the axis 4023. Therefore also several such printing heads can be aligned along the axis 4023 or on axis parallel to it in order to realize fast and efficient production. The printing heads can be controlled simultaneously and synchronously, or they can be controlled individually, to be able to move them independently of each other.

What is claimed is:

1. A device for manufacturing multi-layered products with individual geometry, the device comprising:
   a substrate plate;
   a material application device movable relative to the substrate plate for application of material above the substrate plate, wherein the material application device comprises a printing head for applying the material in a three-dimensional printing process, a contour crafting process, a fused deposition modeling process, a laminated object modeling process, a polyamide casting process or a multi jet modeling process; and
   a control device for transmitting signals to the material application device and/or a conveyor device for conveying the substrate plate, wherein the control device is adapted to control the material application device such that it dispenses the material selectively on predetermined regions corresponding to the cross-section of the product in the respective layer; wherein the material application device is adapted to apply the material in a plane, the plane aligned at an oblique angle relative to the surface of the substrate plate on which the material is applied.

2. The device according to claim 1, wherein the substrate plate is divided into a plurality of substrate plate segments;
   the material application device is adapted to simultaneously apply a material layer onto a number of the plurality of substrate plate segments; and
   the substrate plate segments are connectably-detachable with each other or with a base carrier.

3. A device for manufacturing multi-layered products with individual geometry, the device comprising:
   a substrate plate;
   a material application device movable relative to the substrate plate for application of material above the substrate plate; and
   a control device for transmitting signals to the material application device and/or a conveyor device for conveying the substrate plate, wherein the control device is adapted to control the material application device such that it dispenses the material selectively on predetermined regions corresponding to the cross-section of the product in the respective layer; wherein the material application device is adapted to apply the material in a plane, the plane aligned at an oblique angle to a surface of the substrate plate on which the material is applied;
   wherein the substrate plate comprises a plurality of substrate plate segments which are arranged on an endless conveyor belt running partially or completely in a processing chamber, the chamber at least partially sealed in a controlled atmosphere during use, wherein the control device is adapted to produce a relative movement between the substrate plate segments and the material application device in a direction substantially parallel to the surface of the substrate plate segments after a layer of the material was applied.

4. The device according to claim 1, wherein the substrate plate is adapted to be moved in a horizontal direction after a layer of material is applied to the product.

5. A device for manufacturing products with individual geometry and multiple layers, the device comprising:
   a substrate plate coupled to a substrate carrier;
   a material application device, wherein at least one of the material application device and the substrate plate is movable relative to the other, the material application device configured to apply material above the substrate plate, wherein the material application device comprises a printing head for applying the material in a three-dimensional printing process, a contour crafting process, a fused deposition modeling process, a laminated object modeling process, a polyamide casting process or a multi jet modeling process; and
   a control device coupled with the material application device, the control device capable of transmitting signals; wherein the control device is adapted to control the material application device such that the material application device dispenses material selectively onto predetermined regions, the regions corresponding to a cross-section of the product in the respective layer; wherein the substrate plate is divided into a plurality of substrate plate segments, the segments connectably-detachable with each other or with the substrate carrier, wherein the control device is further adapted to manufacture several products distributed over several substrate plate segments and to adjust the heights of the substrate segments in relation to each other such that the products can be produced in different stages of manufacturing on different substrate plate segments, wherein the substrate carrier forms an endless conveyor device and that the material application device is adapted to dispense the material directly onto the substrate carrier and/or that a separation device is arranged at the substrate carrier to detach manufactured products after their completion from the substrate carrier or from the substrate plate arranged thereon.

6. The device according to claim 5, wherein the control device is adapted to control the material application device and/or the endless conveyor device in such a way that a layer with a thickness between about 5 µm and 200 µm is applied during use.

7. The device of claim 1, wherein the material application device is adapted to apply the material at an angle smaller or equal to a dumping angle of the material on a surface of the substrate on which the material is applied.

8. A device for manufacturing multi-layered products with individual geometry, the device comprising:
   a substrate plate;
   a material application device movable relative to the substrate plate for application of material above the substrate plate; and
   a control device for transmitting signals to the material application device and/or a conveyor device for conveying the substrate plate, wherein the control device is adapted to control the material application device such that it dispenses the material selectively on predetermined regions corresponding to the cross-section of the product in the respective layer,
   wherein the control device and the application device are adapted to manufacture a three-dimensional product by means of an additive manufacturing method excluding the LENS process, wherein the material application device is adapted to apply the material in a plane, the plane aligned at an oblique angle relative to a surface of the substrate plate on which the material is applied, wherein the control device is adapted to produce a relative movement between the substrate plate and the material application device in a direction parallel to the surface of the substrate plate after a layer of the material was applied.

9. The device according to claim 3, wherein the substrate plate is moved relative to the material application device.

10. The device according to claim 3, wherein the material application device is moved relative to the substrate plate.

11. The device according to claim 5, wherein the endless conveyor device is turned around at a deflecting device and deformed so as to cause the products to detach from the endless conveyor device.

* * * * *